US012622923B2

(12) United States Patent (10) Patent No.: US 12,622,923 B2

Washington et al. (45) Date of Patent: *May 12, 2026

(54) HEALTH BENEFITING COMPOSITIONS OF DAILY NUTRITION AND METHODS OF USE THEREOF

(71) Applicant: Uplifting Results Labs, Inc., Los Angeles, CA (US)

(72) Inventors: Marc Washington, Los Angeles, CA (US); Ren-Hau Lai, Torrance, CA (US); Mengyu Zhao, Inglewood, CA (US)

(73) Assignee: Uplifting Results Labs, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/669,326

(22) Filed: May 20, 2024

(65) Prior Publication Data

US 2024/0307432 A1 Sep. 19, 2024

Related U.S. Application Data

(63) Continuation of application No. 17/706,270, filed on Mar. 28, 2022, now Pat. No. 12,023,350, which is a continuation of application No. 16/825,628, filed on Mar. 20, 2020, now Pat. No. 11,318,159.

(51) Int. Cl.
| | |
|---|---|
| *A61K 31/718* | (2006.01) |
| *A23L 33/115* | (2016.01) |
| *A23L 33/185* | (2016.01) |
| *A23L 33/22* | (2016.01) |
| *A61K 9/00* | (2006.01) |
| *A61K 38/00* | (2006.01) |

(52) U.S. Cl.
CPC .......... *A61K 31/718* (2013.01); *A23L 33/115* (2016.08); *A23L 33/185* (2016.08); *A23L 33/22* (2016.08); *A61K 9/0056* (2013.01); *A61K 38/00* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 11,318,159 | B2 | 5/2022 | Washington et al. |
| 2014/0044844 | A1 | 2/2014 | Somavat et al. |

FOREIGN PATENT DOCUMENTS

| | | |
|---|---|---|
| CN | 108523134 A | 9/2018 |
| KR | 10-1649388 B1 | 8/2016 |
| WO | 2014/028491 A1 | 2/2014 |

OTHER PUBLICATIONS

Behall et al., "Consumption of Both Resistant Starch and β-Glucan Improves Postprandial Plasma Glucose and Insulin in Women," Diabetes Care 29 (5): 976-981 (2006).
Sajilata et al., "Resistant Starch—A Review," Comprehensive Reviews in Food Science and Food Safety 5: 1-17 (2006).
English, "Huel Review—A Vegan Meal Replacement High in Omega-3?" barbend.com; https://barbend.com/huel-review/ (Nov. 11, 2019).
"How many oz. of water for 1 scoop?" Huel.com; https://discourse.huel.com/t/how-many-oz-of-water-for-1-scoop/2762 (Aug. 2018).
Watson, "Resistant starch . . . unsung hero?" Food Navigator USA; https://www.foodnavigator-usa.com/Article/2019/06/11/Resistant-starch-unsung-hero-for-digestive-health-blood-glucose-management-and-weight-control (Jun. 11, 2019).
Du et al., "A Concise Review on the Molecular Structure and Function Relationsip of β-Glucan," International Journal of Molecular Sciences 20(16): 4032 (2019).
Gunnars, "Resistant Starch 101—Everything You Need to Know," <https://www.healthline.com/nutrition/resistant-starch-101#types> (Jul. 2018).
English, "Huel Review—A Vegan Meal Replacement High in Omega-3?," <https://barbend.com/huel-review/> (Nov. 2019).
Watson, "Resistant starch . . . unsung hero?," <https:///foodnavigator-usa.com/Article/2019/06/11/Resistant-starch- unsung-hero-for-digestive-health-blood-glucose-management-and-weight-control> (Jun. 2019).

*Primary Examiner* — Anand U Desai
*Assistant Examiner* — Jacob A Boeckelman
(74) *Attorney, Agent, or Firm* — Cozen O'Connor

(57) ABSTRACT
The disclosure relates to a fiber blend for a health benefiting nutrition formulation, comprising: a resistant starch obtained from one or more sources selected from the group consisting of green banana resistant starch, maize or corn resistant starch, and potato resistant starch, the resistant starch having a resistant starch weight; an oat beta glucan having a beta glucan weight; and a maize or corn resistant dextrin having a resistant dextrin weight. The ratio of [the resistant starch weight]:[the beta glucan weight]:[the resistant dextrin weight]=1:0.15-4:0.15-4.

20 Claims, 6 Drawing Sheets

| Vanilla Flavor | | |
|---|---|---|
| Ingredient | Amount (g) | |
| | 1 serving | Active Ingredient | W/W proportions of active ingredients |
| milk protein concentrate (MPC) (purity: 85 w%) | 9.25-27.75 | 7.9-23.58 (Protein) | 1 (Protein)* |
| Green banana RS (purity: 64.4 w%) | 2.95-8.85 | 1.8-5.7 (Fiber) | 0.076-0.72 (Fiber) |
| Maize RS (purity: 48.3 w%) | 2.9-8.7 | 1.4-4.2 (Fiber) | 0.059-0.53 (Fiber) |
| Oat Beta Glucan fiber (purity: 76.2 w%) | 2.6-7.9 | 1.98-6 (Fiber) | 0.084-0.76 (Fiber) |
| resistant dextrin (purity: 90 w%) | 2.5-7.5 | 2.25-6.7 (Fiber) | 0.095-0.85 (Fiber) |
| Sunflower Oil Powder (purity: 70%) | 3.5-10.5 | 2.45-7.35 (Fat) | 0.104-0.93 (Fat) |
| Vitamin mixture | 2.50 | | |
| flavor agent | | | |
| Non-glucose sweetener | | | |
| Anti-Foaming Agent | | | |
| Thickener | | | |
| Water (fl oz) | 5-20 | | |

*total amount of protein is set to unity.

FIG. 1. Example I.

| Chocolate Flavor | | | |
|---|---|---|---|
| Ingredient | Amount (g) | | |
| | 1 serving | Active Ingredients | W/W proportion of active ingredients |
| Instantized MPC 85% | 9.25-27.75 | 7.9-23.58 (Protein) | 1 (Protein)* |
| Green banana RS (purity: 64.4 w%) | 2.95-8.85 | 1.8-5.7 (Fiber) | 0.72-0.076 (Fiber) |
| Maize RS (purity: 48.3 w%) | 2.9-8.7 | 1.4-4.2 (Fiber) | 0.53-0.059 (Fiber) |
| Oat Beta Glucan (purity: 76.2 w%) | 2.6-7.9 | 1.98-6 (Fiber) | 0.76-0.084 (Fiber) |
| Resistant dextrin (purity: 90 w%) | 2.5-7.5 | 2.25-6.7 (Fiber) | 0.85-0.095 (Fiber) |
| Sunflower Oil Powder (purity: 70%) | 3.5-10.5 | 2.45-7.35 (Fat) | 0.93-0.104 (Fat) |
| Vitamin mixture | | | |
| flavor agent | | | |
| Non-glucose sweetener | | | |
| Anti-Foaming Agent | | | |
| Thickener | | | |
| Water (fl oz) | 5-20 | | |

*total amount of protein is set to unity.

FIG. 2. Example II.

| Mocha Latte Flavor | | | |
|---|---|---|---|
| Ingredient | Amount (g) | | W/W proportion of active ingredients |
| | 1 serving | Active Ingredients | |
| Instantized MPC 85% | 9.25-27.75 | 7.9-23.58 (Protein) | 1 (Protein)* |
| Green banana RS (purity: 64.4 w%) | 2.95-8.85 | 1.8-5.7 (Fiber) | 0.72-0.076 (Fiber) |
| Maize RS (purity: 48.3 w%) | 2.9-8.7 | 1.4-4.2 (Fiber) | 0.53-0.059 (Fiber) |
| Oat Beta Glucan (purity: 76.2 w%) | 2.6-7.9 | 1.98-6 (Fiber) | 0.76-0.084 (Fiber) |
| Resistant dextrin (purity: 90 w%) | 2.5-7.5 | 2.25-6.7 (Fiber) | 0.85-0.095 (Fiber) |
| Sunflower Oil Powder (purity: 70%) | 3.5-10.5 | 2.45-7.35 (Fat) | 0.93-0.104 (Fat) |
| Vitamin mixture | | | |
| flavor agent | | | |
| Non-glucose sweetener | | | |
| Anti-Foaming Agent | | | |
| Thickener | | | |
| Water (fl oz) | 5-20 | | |

*total amount of protein is set to unity.

FIG. 3. Example III

| Chocolate Flavor | | | |
|---|---|---|---|
| Ingredient | Amount (g) | | W/W proportion of active ingredients |
| | 1 serving | Active Ingredients | |
| Non-animal protein (purity: 80 w%) (a blend of bean, grain, and/or seed proteins) | 5-25 | 4-20 (Protein) | 1 (Protein)* |
| Green banana RS (purity: 64.4 w%) | 3-7 | 1.92-4.48 (Fiber) | 0.1-1.12 (Fiber) |
| Maize RS (purity: 48.3 w%) | 3-7 | 1.45-3.38 (Fiber) | 0.073-0.845 (Fiber) |
| Oat Beta Glucan (purity: 76.2 w%) | 3-7 | 2.28-5.33 (Fiber) | 0.114-1.33 (Fiber) |
| Resistant dextrin (purity: 90 w%) | 3-7 | 2.7-6.3 (Fiber) | 0.135-1.575 (Fiber) |
| Sunflower Oil Powder (purity: 70%) | 5-9 | 3.5-6.3 (Fat) | 0.175-1.58 (Fat) |
| Vitamin mixture | | | |
| flavor agent | | | |
| Non-glucose sweetener | | | |
| Anti-Foaming Agent | | | |
| Thickener | | | |
| Water (fl oz) | 5-20 | | |

*total amount of protein is set to unity.

FIG. 4.  Example IV.

Blood sugar results of each time point on day 0, 7, 14, and 21. *P<0.05.

| Name | Day 0 - regular breakfast | | | | Day 7 - shake | | | | Day 14 - shake | | | | Day 21 - shake | | | | Average (7,14,21 days) | | | |
|---|---|---|---|---|---|---|---|---|---|---|---|---|---|---|---|---|---|---|---|---|
| | T-0 | T+30 | T+60 | T+120 | T-0 | T+30 | T+60 | T+120 | T-0 | T+30 | T+60 | T+120 | T-0 | T+30 | T+60 | T+120 | T-0 | T+30 | T+60 | T+120 |
| Subject 1 | 135 | 129 | 125 | 118 | 112 | 129 | 136 | 109 | 120 | 140 | 124 | 100 | 127 | 145 | 117 | 120 | 120 | 138 | 126 | 110 |
| Subject 2 | 112 | 94 | 106 | 112 | 106 | 116 | 106 | 104 | 100 | 106 | 103 | 101 | 86 | 104 | 111 | 116 | 97 | 109 | 107 | 107 |
| Subject 3 | 112 | 112 | 212 | 191 | 103 | 112 | 123 | 215 | 102 | 111 | 125 | 142 | 103 | 105 | 117 | 124 | 103 | 109 | 122 | 160 |
| Subject 4 | 78 | 93 | 112 | 97 | 92 | 87 | 110 | 112 | 100 | 90 | 86 | 84 | 109 | 94 | 87 | 85 | 100 | 90 | 94 | 94 |
| Subject 5 | 83 | 91 | 103 | 99 | 79 | 111 | 90 | 100 | 88 | 84 | 81 | 105 | 103 | 111 | 97 | 106 | 90 | 102 | 89 | 104 |
| Subject 6 | 160 | 193 | 245 | 202 | 135 | 168 | 137 | 128 | 152 | 149 | 156 | 140 | 179 | 187 | 185 | 157 | 155 | 168 | 159 | 142 |
| Subject 7 | 107 | 148 | 132 | 117 | 110 | 152 | 161 | 111 | 101 | 132 | 127 | 115 | 98 | 126 | 118 | 111 | 103 | 137 | 135 | 112 |
| Subject 8 | 85 | 77 | 82 | 72 | 85 | 84 | 80 | 80 | 94 | 114 | 105 | 106 | 105 | 86 | 92 | 85 | 95 | 95 | 92 | 90 |
| Subject 9 | 90 | 105 | 110 | 99 | 100 | 91 | 97 | 91 | 89 | 99 | 92 | 93 | 96 | 91 | 92 | 88 | 95 | 94 | 94 | 91 |
| Subject 10 | 100 | 140 | 99 | 93 | 116 | 107 | 97 | 95 | 111 | 114 | 97 | 95 | 112 | 96 | 95 | 110 | 113 | 106 | 96 | 100 |
| Subject 11 | 87 | 103 | 122 | 130 | 86 | 97 | 109 | 118 | 97 | 105 | 118 | 123 | 93 | 107 | 115 | 128 | 92 | 103 | 114 | 123 |
| Subject 12 | 100 | 140 | 146 | 108 | 105 | 97 | 108 | 95 | 98 | 105 | 106 | 102 | 93 | 85 | 117 | 104 | 99 | 96 | 110 | 100 |
| Subject 13 | 93 | 182 | 145 | 123 | 88 | 77 | 77 | 68 | 80 | 102 | 92 | 85 | 79 | 92 | 88 | 82 | 82 | 90 | 86 | 78 |
| Subject 15 | 86 | 109 | 99 | 90 | 94 | 96 | 97 | 108 | 122 | 109 | 110 | 92 | 99 | 115 | 97 | 94 | 105 | 107 | 101 | 98 |
| Subject 17 | 66 | 117 | 103 | 100 | 94 | 93 | 87 | 84 | 89 | 86 | 86 | 83 | 101 | 95 | 87 | 87 | 95 | 91 | 87 | 85 |
| Subject 21 | 84 | 112 | 98 | 83 | 102 | 157 | 94 | 128 | 97 | 98 | 87 | 76 | 109 | 110 | 97 | 91 | 103 | 122 | 93 | 98 |
| | | | | | | | | | | | | | | | | | | | | |
| Average | 99 | 122 | 127 | 115 | 100 | 111 | 107 | 109 | 103 | 109 | 106 | 103 | 106 | 109 | 107 | 106 | 103 | 110 | 107 | 106 |
| Student's T test, one tailed, P value | | | | | 0.4 | 0.16 | 0.052 | 0.325 | 0.3 | 0.098 | 0.041 | 0.121 | 0.19 | 0.123 | 0.055 | 0.189 | 0.28 | 0.116 | 0.047 | 0.1974 |

FIG. 6

HEALTH BENEFITING COMPOSITIONS OF DAILY NUTRITION AND METHODS OF USE THEREOF

This application is a continuation of U.S. patent application Ser. No. 17/706,270, filed Mar. 28, 2022, which is a continuation of U.S. patent application Ser. No. 16/825,628, filed on Mar. 20, 2020, now U.S. Pat. No. 11,318,159, both of which are herein incorporated by reference in their entirety.

FIELD OF THE DISCLOSURE

The instant disclosure relates generally to health benefiting daily nutrition. More specifically, this disclosure relates to embodiments of daily nutrition with specific formulations of protein, fiber, and fat that are adapted for various health benefits, including but not limited to, blood sugar management, digestive health, and weight management.

BACKGROUND

Diabetes, a group of metabolic disorders characterized by high blood sugar level over a prolonged period of time, are mostly related to insulin irregularity. The medical community classified two types of diabetes. Type 1 diabetes results from the pancreas's failure to produce enough insulin due to loss of beta cells. This form was referred to as "insulin-dependent diabetes mellitus" (IDDM) or "juvenile diabetes." The loss of beta cells is caused by an autoimmune response. The cause of this autoimmune response is unknown. Type 2 diabetes begins with insulin resistance, a condition in which cells fail to respond to insulin properly. As the disease progresses, a lack of insulin may also develop. This form was referred to as "non-insulin-dependent diabetes mellitus" (NIDDM) or "adult-onset diabetes". The most common cause is a combination of excessive body weight and insufficient exercise. The group of people that can benefit from the embodiments disclosed herein include both types of diabetes patients.

Carbohydrates are converted to sugar by the digestive process. Cells absorb this sugar in order to support life. Insulin, a hormone produced by the pancreas, is key to the absorption of sugar by the cells. Without this hormone being present, the cells will not absorb the sugar, and will die. The medical community uses a scale of 0 to 540 mg/dl to represent the amount of sugar in the blood. Low blood sugar is considered to be 0-70 mg/dl. Normal blood sugar is considered 70-126 mg/dl. High blood sugar is in the range 126-200 mg/dl. Very high blood sugar is over 200 mg/dl.

Below 70 mg/dl is a condition known as very low blood sugar (hypoglycemia). This is the level at which brain damage and death can occur if immediate action is not taken to correct the situation. At 200 mg/dl and above is a condition known as very high blood sugar (hyperglycemia). As the sugar level approaches 540 mg/dl, brain damage and death can occur if immediate corrective action is not taken. At both ends of the spectrum, very high and very low, a diabetic will go into a coma.

To correct a very low blood sugar condition, it is necessary to get sugar into the blood immediately, by ingesting sugar or its equivalent: for example, a high-sugar fruit juice such as orange juice.

To correct a very high sugar condition, only insulin can help. Even quick-acting insulin still takes hours to reduce a high sugar condition. It is, therefore, easier to deal with low blood sugar than high blood sugar.

Per CDC definition, normal blood sugar levels are between 80 and 130 mg/dl before meal, and less than 180 mg/dl two hours after the start of the meal. Between 180 and over 500 is the territory of the diabetic sufferer. Long-term sugar levels in this range will cause blindness, kidney failure and nerve damage, as well as increasing the risk of heart attacks fourfold. Allowing sugar to go over 180 mg/dl is dangerous because at that point excess sugar will be flushed from the blood, and out through the kidneys with urine. This level of 180 mg/dl is known in medical terms as the "renal threshold" with the word "renal" meaning "kidney". In other words, the sugar spills from the blood, through the kidney and into the bladder.

SUMMARY

The instant disclosure relates generally to health benefiting daily nutrition. More specifically, this disclosure relates to embodiments of daily nutrition with specific formulations of protein, fiber, and fat that are adapted for, at least, blood sugar control, digestive health, and weight management. The embodiments provide weight control and blood sugar control by effective management of blood sugar levels within healthy range, improving satiation and satiety, increasing insulin sensitivity, promoting balanced and healthy gut microbiome, and support digestive health.

It is noted that all formulations of the daily nutrition disclosed herein can be in the form of food including but not limited to powders, snacks, and drinks, and in the form of supplements including but not limited to capsules and tablets. For example, the daily nutrition disclosed herein can be prepared as packaged powders that can be added to water to make ready-to-drink shakes. In another example, the daily nutrition disclosed herein can be mixed with meals, snacks, treats, etc. In another example, the daily nutrition disclosed herein can be made as bottle drinks.

The formulation of the health benefiting daily nutrition includes particular proportion among proteins, fibers, and potentially fats. A function of such particular proportion among protein, fiber, and fat is to provide the sense of satisfaction after consumption. With the sense of satisfaction, the craving for additional food and sugar can be reduced. Therefore, a person using the health benefiting daily nutrition disclosed herein will consume less food and less sugar compared to his/her regular consumption thereof without using the health benefiting daily nutrition, achieving the effect of lowing the blood sugar level and losing weight. Thus, the health benefiting daily nutrition can be useful for a person who wants to control the blood sugar level and/or lose weight.

The formulation of the health benefiting daily nutrition improves digestive health. It is designed to be well tolerated by human digestive system, e.g., more than 1-2 servings a day. It is designed to be easy to formulate into most applications, e.g., different drinks, cooking, dishes, snacks, etc. It is designed to be highly soluble in beverages, with less notes of grainy texture.

The formulation of the health benefiting daily nutrition is designed to be satiety and beneficial for blood sugar control and weight management. For example, in one embodiment, one serving as a meal may delay hunger and lower the stimulation of appetite regulating hormones. The formulation of the health benefiting daily nutrition reduces cravings in meal replacement beverages and bars. The health benefiting daily nutrition can be formulated in satiety-oriented snacks and baked goods. The health benefiting daily nutrition can also be formulated in the forms of powder, beverage, cookie, dissert, snack bar, bread, pudding, bakery products, or the like. The health benefiting daily nutrition helps mask off notes arising from high proteins. The formulation of the health benefiting daily nutrition is designed to reduce blood sugar level. In one embodiment, consuming 1 g of resistant dextrin of soluble corn fiber adds merely 0.02 g sugar into the digestive system.

The fibers described in this disclosure means dietary fibers that include resistant starch, beta-glucan, and resistant dextrin. Resistant starch is a kind of starch that resists digestion in the small intestine. Starches that are able to resist the digestion will arrive at the colon where they will be fermented by the gut microbiota, producing a variety of products which include short chain fatty acids that can provide a range of physiological benefits. There are several factors that could affect the resistant starch content of a carbohydrate which includes the starch granule morphology, the amylose-amylopectin ratio and its association with other food component. Resistant starch can be a prebiotic, which stimulates the growth or increases the activities of one or a number of beneficial bacteria in the colon. A resistant starch can be a prebiotic that includes the followings functions: resistance to the upper gastrointestinal environment, fermentation by the intestinal microbiota and selective stimulation of the growth and/or activity of the beneficial bacteria.

Human gastrointestinal microbiota, also known as gut flora or gut microbiota, means the ecosystem of microorganisms that live in the digestive tracts of humans. About 100 trillion bacteria, both good and bad, live inside of digestive system of human body. The gut microbiota influences a person's health condition significantly, as science has shown the potential of healthy gut microbiota on improving immune system functionality, reducing the risk of heart diseases, reducing body inflammation, inhibiting the growth of cancer cells, etc. The daily nutrition disclosed herein is beneficial to human gastrointestinal microbiota.

Gut microbiota is associated with rheumatoid arthritis (RA). Studies show gut bacteria may predict susceptibility to RA as well as offer a possible solution. Researchers were able to isolate certain bacteria that are high in RA patients, but low in healthy individuals. Studies also found that mice treated with the bacterium *Prevotella histicola* had less severe and less frequent symptoms and fewer inflammatory conditions associated with RA. The daily nutrition disclosed herein is beneficial to human gastrointestinal microbiota.

Gut microbiota is associated with cancer. Studies show evidence that a particular strain of the bacterium *Lactobacillus johnsonii* may protect against some cancers. Scientists gave mice a mutation that is associated with a high incidence of leukemia, lymphomas, and other cancers. When treated with the bacterium, the mice developed lymphoma only half as quickly compared with a control group. The daily nutrition disclosed herein is beneficial to human gastrointestinal microbiota.

Gut microbiota is associated with heart disease. Research found the bacterial strain *Akkermansia muciniphila* could prevent inflammation that contributes to fatty plaque buildup in arteries. Scientists believe the effect was due to a protein that blocks communication between cells in the inner lining of the gut. As a result, fewer toxins from a poor diet could pass into the bloodstream, which in turn reduced inflammation. The daily nutrition disclosed herein is beneficial to human gastrointestinal microbiota.

Gut microbiota is associated with the immune system. Studies found that introducing a particular bacterial strain into the digestive tracts of mice with melanoma prompted their immune systems to attack tumor cells. The gains were comparable to treatment with anti-cancer drugs called checkpoint inhibitors. The daily nutrition disclosed herein is beneficial to human gastrointestinal microbiota.

Gut microbiota is associated with emotion via gut-brain axis. The gut-brain axis, a bidirectional neurohumoral communication system, is important for maintaining homeostasis and is regulated through the central and enteric nervous systems and the neural, endocrine, immune, and metabolic pathways, and especially including the hypothalamic-pituitary-adrenal axis (HPA axis). It has been shown that there is correlation between gut microbiota and anxiety disorders and mood disorders. Attempts have been made to influence emotions using prebiotics and probiotics. The daily nutrition disclosed herein is beneficial to human gastrointestinal microbiota.

The health benefiting daily nutrition disclosed herein includes fat, also known as lipid, or fatty acids. Fatty acids play important physiological functions. They are the building blocks of phospholipids and glycolipids, crucial components of cell membranes. Fatty acids are the best biological fuel molecules, capable of yielding more than twice as much energy per gram as produced by carbohydrate or protein. Fatty acids directly affect the functions of many proteins through covalent modifications of such proteins. Fatty acids also affect membrane fluidity and associated cellular processes. Fatty acids are also involved in gene regulation, as such may be used to optimize expression of certain genes. Fatty acids' derivatives are also important hormones and biological messengers, e.g., prostaglandins, thromboxane, leukotrienes, lipoxins, and resolvins. These hormones and messengers affect a broad range of physiological functions such as vasal dilation, platelets aggregation, pain modulation, inflammation, and cell growth.

Fatty acids included in the health benefiting daily nutrition disclosed herein also increases the sense of satisfaction, which reduces the overall intake of food for users. In another aspect, the composition comprises one or more of the following components: peanut oil, vegetable oil, avocado oil, olive oil, sunflower oil, safflower oil and/or flaxseed oil. In yet another aspect, the composition further comprises one or more of the following components: mustard oil, palm oil, and soybean lecithin.

The health benefiting daily nutrition disclosed herein provides a particular proportion among proteins, fibers, and/or fats promoting the growth of good bacterium and inhibiting bad ones. As a result, the gut microbiota is improved. Thus, using the health benefiting daily nutrition disclosed herein may improve the gut microbiota which have the potential to improve various health conditions, including heart disease, arthritis, cancer, and immune system.

Embodiments of using the health benefiting daily nutrition include a method of prophylaxis or treatment of a medical condition for a mammalian subject, said method comprising administering a therapeutically effective amount of the composition of any of the above embodiment to said subject, wherein said medical condition is linked with overweight, immune system functionality, heart disease, blood sugar imbalance, diabetics, lipid imbalance in said mammalian subject. In one aspect, said medical/physical condition is selected from the group consisting of: a symptom of menopause, a cardiovascular disease, a mental disorder, a neural disorder, a musculoskeletal disorder, an endocrine disorder, a cancer, a digestive system disorder, a symptom of aging, a viral infection, a bacterial infection, obesity, overweight, a renal disease, a pulmonary disorder, an ophthalmologic disorder, a dermatological disorder, a sleep disorder, a dental disease, an immune system disease, and an autoimmunity.

In one embodiment according to the disclosure, a health benefiting daily nutrition includes protein, fiber, and fat with a w/w ratio of 1:0.2-5:0-3, wherein each of the fiber and protein is more than 5 g. In one embodiment, the protein, fiber, and fat (g) are 5-25:5-25:0-15.

In one embodiment according to the disclosure, a health benefiting daily nutrition includes protein, fiber, and fat with a w/w ratio of 1:0.25-1.5:0, wherein each of fiber and protein is more than 5 g. For example, the composition of matter includes (g) proprietary vegan protein blend 15 and proprietary prebiotic fiber blend 15. In this example, the proteins are from non-animal sources.

In one embodiment according to the disclosure, a health benefiting daily nutrition includes protein, fiber, and fat with a w/w ratio of 1:0.25-1.5:0.1-0.5, wherein each of the fiber and protein is more than 5 g. For example, the composition of matter includes (g) vegan protein blend 15, proprietary prebiotic fiber blend 15, and sunflower oil powder 4.5. In this example, the proteins are from non-animal sources.

In one embodiment according to the disclosure, a health benefiting daily nutrition includes protein, fiber, and fat with a w/w ratio of 1:0.25-1.5:0, wherein each of the fiber and protein is more than 5 g. For example, the composition of matter includes (g) dairy protein 15, proprietary prebiotic fiber blend 15 including resistant starch, oat beta glucan, and resistant dextrin at the ratio of 1:0.1-2:0.1-2. In this example, the protein is from animal, i.e., dairy protein.

In one embodiment according to the disclosure a formulation of the health benefiting daily nutrition includes protein, fiber, and fat with a w/w ratio of 1:0.5-2:0, wherein a total weight of fiber is more than 5 g.

In one embodiment according to the disclosure, a formulation of the health benefiting daily nutrition includes protein, fiber, and fat with a w/w ratio of 1:0.5-2:0.1-1, wherein a total weight of fiber is more than 5 g.

In one embodiment according to the disclosure, a method of using a health benefiting daily nutrition includes, opening the package that contains the health benefiting daily nutrition and mixing the health benefiting daily nutrition with a solvent. The health benefiting daily nutrition includes protein and fiber, with a w/w ratio of 1:0.5-2, wherein a total weight of fiber is more than 5 g. The solvent can be water, dairy product, juice, tea, soft drinks, plant based/alternative dairy, etc.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the concepts and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed systems and methods, reference is now made to the following descriptions taken in conjunction with the accompanying drawings.

FIG. 1 shows a formulation of a health benefiting daily nutrition including animal protein and vanilla flavor according to one embodiment of the disclosure.

FIG. 2 shows a formulation of a health benefiting daily nutrition including animal protein and chocolate flavor according to one embodiment of the disclosure.

FIG. 3 shows a formulation of a health benefiting daily nutrition including vegetable protein and mocha latte flavor according to one embodiment of the disclosure.

FIG. 4 shows a formulation of a health benefiting daily nutrition including vegetable protein and mocha latte flavor according to one embodiment of the disclosure.

FIG. 6 shows a table of clinical data of each individual test subjects using one embodiment of the disclosure.

DETAILED DESCRIPTION

Figure 5:
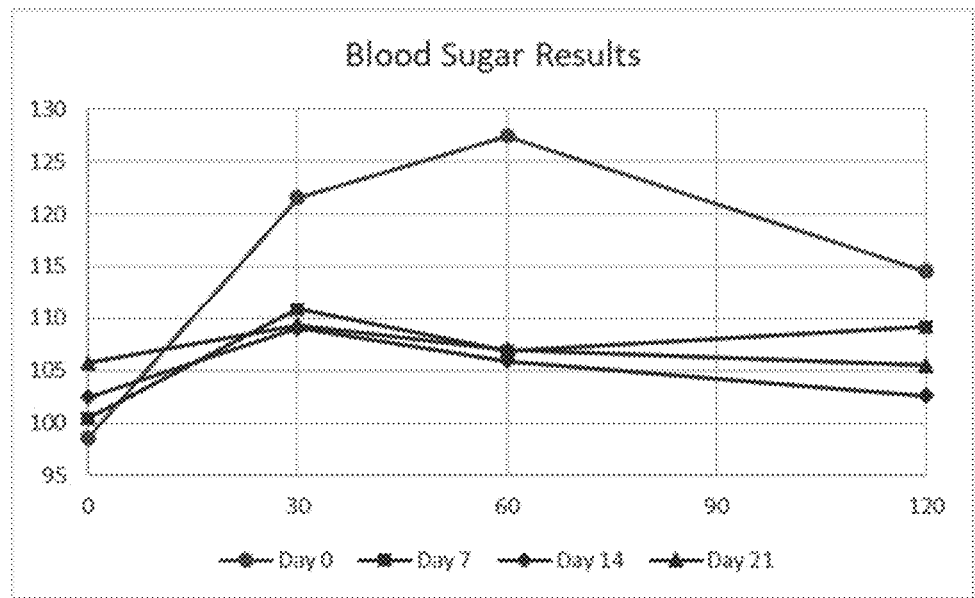
FIG. 5 shows clinical data related to the blood glucose control using one embodiment of the disclosure.

"Protein" used in this disclosure may be proteins obtained from any source, including animal and plant. Protein used in this disclosure can be from animal, such as meat, egg, milk, organs, tissues, etc. Protein used in this disclosure can also be plant based, such as, beans, soybean, lupine, pea, chickpea, lentil, bean and potato, etc.

"Fiber" used in this disclosure means dietary fiber known to a person skilled in the art. Dietary fiber is a kind of non-digestible and/or difficult-to-digest carbohydrate. Dietary fiber consists of non-starch polysaccharides and other plant components such as cellulose, resistant starch, resistant dextrins, inulin, lignins, chitins, pectins, beta-glucans, and oligosaccharides. As one of prebiotic dietary fibers, resistant starch can be fermented by the large intestinal microbiota, conferring benefits to human health through the production of short-chain fatty acids, increased beneficial bacterial mass, and promotion of butyrate-producing bacteria. Resistant starch has some of the same physiologic effects as dietary fiber, which functions as a mild laxative.

In particular, the fiber in this disclosure can be in a particulate form such, preferably comprising more than 75 wt % particles having a size of 30-297 micron (US mesh #50-#400). Suitable sources for fiber include banana (green, yellow, and/or ripped), potato, yam, cereals, for instance corn, wheat, rice, and tapioca and beans or pulses. In one embodiment, the resistant starch included in this disclosure is mixed with water under the gelatinization temperature. In another embodiment, the resistant starch included in this disclosure is mixed with water above the gelatinization temperature.

The term "consisting essentially of" means that the composition or formulation (a) necessarily includes the listed ingredients and (b) is open to unlisted ingredients that do not materially affect the basic and novel properties of the composition. For example, a resistant starch blend "consisting essentially of" green banana resistant starch and maize resistant starch means the resistant starch blend includes green banana resistant starch and maize resistant starch and is open to unlisted ingredients that do not materially affect the basic and novel properties of the resistant starch blend.

Plants store starch in tightly packed granules, consisting of layers of amylose and amylopectin. The size and shape of the starch granule varies by botanical source. For instance, the average size of potato starch at approximately 38 micrometers, wheat starch an average of 22 micrometers and rice starch approximately 8 micrometers. The following is a short list of resistant starch source and its starch granule size in micrometers: Maize/corn 5-30; waxy maize 5-30; tapioca 4-35; potato 5-100; wheat 1-45; rice 3-8; high amylose maize 5-30.

Raw starch granules resist digestion, i.e., raw bananas, raw potatoes. This does not depend on the amylose or amylopectin content, but rather the structure of the granule protecting the starch. When starch granules are cooked, water is absorbed into the granule causing swelling and increased size. In addition, amylose chains can leak out as the granule swells. The viscosity of the solution increases as the temperature is increased. The gelatinization temperature is defined as the temperature at which maximum gelatinization or swelling of the starch granule has occurred. This is also the point of maximum viscosity. Further cooking will burst the granule apart completely, releasing all of the glucose chains. In addition, viscosity is reduced as the granules are destroyed. Starch consists of amylose and amylopectin which affect the textural properties of manufactured foods. Cooked starches with high amylose content generally have increased resistant starch. The followings is a short list of resistant starch source and its gelatinization temperature in Celsius degrees: Maize/corn 62-72; waxy maize 63-72; tapioca 632-73; potato 59-68; wheat 58-64; rice 68-78; high amylose maize 63-92.

In one embodiment, the resistant starch can be from rice. The weight percentage, based on total weight, for resistant starch usually is 40 wt. % or less, in particular 3-35 wt. %.

Bran, especially outer tissues of the kernel, including pericarp from a variety of cereal sources such as wheat, maize or corn, oats, rice, pea and other pulses, barley, triticale, sorghum, milo, potato, tapioca, cassava, sago and other plant extracts have been used as fiber sources.

More recently, resistant starches have been approved as a source of dietary fiber by FDA. Resistant starches are starches that are highly resistant to hydration and, when ingested, pass through the upper regions of the gastrointestinal tract largely unchanged.

Green bananas and raw potatoes include significant amount of resistant starch. Such resistant starch sources have gelatinization temperatures that are typically on the order of about 60° C. to about 80° C. In one embodiment, the resistant starch included in this disclosure is mixed with water under the gelatinization temperature. In another embodiment, the resistant starch included in this disclosure is mixed with water above the gelatinization temperature. It is also possible to produce resistant starch by extensively processing, namely repeatedly cooking and cooling, starch pastes.

Corn and maize can be a suitable source of fiber and resistant starch. Any high amylose starch from corn and/or maize can be used in the embodiments disclosed herein. The maize starch is preferably derived from any single maize hybrid, any double maize hybrid, or any multiple cross maize hybrid, with a maize single cross hybrid that is capable of producing maize having a high amylose content being preferred. Some suitable, though non-exhaustive, examples of high amylose starch are the maize RS high amylose starches commercially available. Maize RS starch can be used in the present invention.

While maize starch is suitable as the resistant starch, any other resistant starch may be utilized to achieve gut microbiota benefits of the embodiment disclosed herein. For example, resistant waxy maize (corn) starch; resistant regular or normal maize (corn) starch; resistant wheat starch; resistant rice starch; resistant legume, pea or pulse starch; resistant barley starch; resistant triticale starch; resistant sorghum starch; resistant milo starch; resistant cassava starch; resistant oat starch; resistant potato starch; resistant yam starch; resistant green banana starch; resistant tapioca starch; and resistant sago starch are some other non-exhaustive examples of resistant starch that may be utilized in the embodiments of the disclosure.

Beta-D-glucans, usually referred to as beta glucans, comprise a class of fiber, indigestible polysaccharides found in nature in sources such as grains, barley, yeast, bacteria, algae and mushrooms. Beta-D-glucans includes high amount of prebiotic dietary fiber. Beta-D-glucans can be used in the embodiments of health benefiting daily nutrition disclosed herein.

In oats, beta glucans are concentrated in the bran, more precisely in the aleurone and sub-aleurone layer. Oat beta glucan is a fiber with rich prebiotic features. Oat beta glucan is richly stored in oat bran produced by removing the starchy content of the grain. Oat beta glucan is rich in dietary fibers, especially in soluble fibers, present in the inner periphery of the kernel. Oats contain more soluble fibers than any other grain, resulting in slower digestion and an extended sensation of fullness, among other things.

Oat is a rich source of the water-soluble fiber (1,3/1,4) β-glucan, and its effects on health have been extensively studied over the last 30 years. Oat beat glucans can be highly concentrated in different types of oat brans. The beta glucan content varies, from 3-5% depending on variety when it grows in the field. Rolled oat/oat flakes is about 4% and whole meal oat flour. With certain kind of oat, concentrations of beta glucans can reach 6-32% (weight percentage). Oat beta glucan is a natural soluble fiber. It is a viscous polysaccharide made up of units of the monosaccharide D-glucose. Oat beta glucan is composed of mixed-linkage polysaccharides. This means the bonds between the D-glucose units are either beta-(1→3) linkages or beta-(1→4) linkages. The (1→3)-linkages break up the uniform structure of the beta-D-glucan molecule and make it hydrophilic, soluble, and flexible. In comparison, the indigestible polysaccharide cellulose is also a beta glucan, but is not soluble. The reason it is insoluble is cellulose consists only of (1→4)-beta-D-linkages.

Oat beta glucan are large molecules. Originally in the oat kernel, it is composed of up to 200,000 glucose units, which gives molecular weights in the range of 1500-3000 kDa.

Beta-D-glucans, usually referred to as beta glucans, comprise a class of indigestible polysaccharides found in nature in sources such as grains, barley, yeast, bacteria, algae and mushrooms. In oats, they are concentrated in the bran, more precisely in the aleurone and sub-aleurone layer.

Studies show that oat and barley beta glucan has cholesterol-lowering properties, especially for the metabolic syndrome. Clinical studies have proved health benefits like avoiding heart diseases by maintaining/lowering cholesterol, decreased blood sugar response after eating—and improving the gut health. In addition, cardiovascular disease has been identified by the World Health Organization as the number one cause of mortality globally. High cholesterol is a risk factor in the development of coronary heart disease.

The latest research demonstrates that oats and oat beta glucan can be recommended as part of a healthy diet to reduce the risk of cardiovascular diseases.

Oats are a naturally rich source of beta-glucan. The effect of oat beta-glucan on both serum cholesterol and blood glucose reduction is proven. Internationally recognized associations, such as the European Society of Cardiology and the US National Cholesterol Education Program, and the recent meta-analysis, support the role of oat beta-glucan, and specifically its viscosity in lowering blood cholesterol levels. It has been established that the consumption of at least 3 g per day of oat beta-glucan can achieve a reduction in LDL cholesterol of up to 10% and reduce the risk of CVD by as much as 20%.

The powders of protein, fiber, and fat used in the embodiments of the health benefiting daily nutritions can have a diameters (in microns): 10-1000, 10-900, 10-800, 10-700, 10-600, 10-500, 10-400, 10-300, 10-200, 10-150, 10-140, 10-130, 10-120, 10-110, 10-100, 10-90, 10-80, 10-70, 10-60, 10-50, 10-40, 10-30, or 10-20.

Example I. Formulation with Dairy Protein

The formulation of example I is shown in FIG. 1. The formulation includes (g): instantized milk protein concentrate (MPC) 9-30, green banana RS (green banana fiber) 2-10, maize RS (maize fiber) 2-10, oat beta glucan (oat fiber) 2-10, and resistant dextrin (corn fiber) 2-10. The formulation also includes sunflower oil powder 2-12 g. The weight of each item referred in this paragraph includes both active ingredient and impure non-active ingredient.

Calculating the active ingredients (considering the purity), In example I, as shown in FIG. 1, fiber blend in w/w proportion of [green banana fiber]:[maize fiber]:[oat fiber]:[corn fiber]=1 (1.8-5.7 g):0.25-2.33 (1.4-4.2 g):0.35-3.33 (1.98-6 g):0.4-4.08 (2.25-7.35 g), setting green banana fiber as unity. In other embodiments, the fiber blend in w/w proportion of [green banana fiber]:[maize fiber]:[oat fiber]:[corn fiber]=1:0-5:0-5:0-5, setting green banana fiber as unity. In other embodiments, the fiber blend in w/w proportion of [green banana fiber]:[maize fiber]:[oat fiber]:[corn fiber]=1:0-4:0-4:0-4, setting green banana fiber as unity. In other embodiments, the fiber blend in w/w proportion of [green banana fiber]:[maize fiber]:[oat fiber]:[corn fiber]=1:0-3:0-3:0-3, setting green banana fiber as unity. In other embodiments, the fiber blend in w/w proportion of [green banana fiber]:[maize fiber]:[oat fiber]:[corn fiber]=1:0-2:0-2:0-2, setting green banana fiber as unity. In yet other embodiments, the fiber blend in w/w proportion of [green banana fiber]:[maize fiber]:[oat fiber]:[corn fiber]=1:0.25-1.75:0.25-1.75:0.25-1.75, setting green banana fiber as unity. In yet other embodiments, the fiber blend in w/w proportion of [green banana fiber]:[maize fiber]:[oat fiber]:[corn fiber]=1:0.5-1.5:0.5-1.5:0.5-1.5, setting green banana fiber as unity. In yet other embodiments, the fiber blend in w/w proportion of [green banana fiber]:[maize fiber]:[oat fiber]:[corn fiber]=1:0.7-1.25:0.75-1.55:0.75-1.25, setting green banana fiber as unity. In yet other embodiments, the fiber blend in w/w proportion of [green banana fiber]:[maize fiber]:[oat fiber]:[corn fiber]=1:0.75-1.25:0.75-1.25:0.75-1.25, setting green banana fiber as unity. It is noted, the green banana fiber mentioned in the above formations can be replaced with beta-glucan soluble fiber, psyllium husk, cellulose, guar gum, pectin, locust bean gum, hydroxypropylmethylcellulose, mixed plant cell wall fibers, arabinoxylan, alginate, inulin, high amylose resistant starch, galactooligosaccharide, polydextrose, resistant maltodextrin, wheat fiber, rice fiber, pea fiber, barley fiber, triticale fiber, sorghum fiber, milo fiber, potato fiber/resistant starch, cassava fiber, sago fiber, sweet potato fiber, yam fiber, bean fiber, grain fiber, fruit fiber, root fiber, etc.

In one embodiment, the w/w proportions of the active ingredients in example I, as shown in FIG. 1, [protein]:[fiber]:[fat]=1:1:0.325, setting [protein] weight as unity.

In other embodiments, the w/w proportion of [protein]:[fiber]:[fat]=1:0.5-2.5:0.05-1, setting [protein] weight as unity. In other embodiments, the w/w proportion of [protein]:[fiber]:[fat]=1:0.6-2.4:0.1-0.9, setting [protein] weight as unity. In other embodiments, the w/w proportion of [protein]:[fiber]:[fat]=1:0.7-2.4:0.1-0.8, setting [protein] weight as unity. In other embodiments, the w/w proportion of [protein]:[fiber]:[fat]=1:0.8-2.3:0.1-0.7, setting [protein] weight as unity. In other embodiments, the w/w proportion of [protein]:[fiber]:[fat]=1:0.9-2.2:0.1-0.6, setting [protein] weight as unity. In other embodiments, the w/w proportion of [protein]:[fiber]:[fat]=1:0.9-2.1:0.1-0.5, setting [protein] weight as unity. In other embodiments, the w/w proportion of [protein]:[fiber]:[fat]=1:0.9-2.0:0.1-0.5, setting [protein] weight as unity. In other embodiments, the w/w proportion of [protein]:[fiber]:[fat]=1:0.9-1.9:0.1-0.4, setting [protein] weight as unity. In other embodiments, the w/w proportion of [protein]:[fiber]:[fat]=1:0.9-1.8:0.1-0.4, setting [protein] weight as unity. In other embodiments, the w/w proportion of [protein]:[fiber]:[fat]=1:0.9-1.7:0.1-0.4, setting [protein] weight as unity. In other embodiments, the w/w proportion of [protein]:[fiber]:[fat]=1:0.9-1.6:0.2-0.4, setting [protein] weight as unity. In other embodiments, the w/w proportion of [protein]:[fiber]:[fat]=1:0.9-1.5:0.2-0.4, setting [protein] weight as unity. In other embodiments, the w/w proportion of [protein]:[fiber]:[fat]=1:0.9-1.4:0.2-0.4, setting [protein] weight as unity. In other embodiments, the w/w proportion of [protein]:[fiber]:[fat]=1:0.9-1.3:0.2-0.4, setting [protein] weight as unity. In other embodiments, the w/w proportion of [protein]:[fiber]:[fat]=1:0.9-1.2:0.25-0.35, setting [protein] weight as unity. In other embodiments, the w/w proportion of [protein]:[fiber]:[fat]=1:0.9-1.1:0.25-0.35, setting [protein] weight as unity.

In other embodiments, [fat] can be omitted. In other embodiments, the w/w proportion of [protein]:[fiber]=1:0.5-2.5, setting [protein] weight as unity. In other embodiments, the w/w proportion of [protein]:[fiber]=1:0.6-2.4, setting [protein] weight as unity. In other embodiments, the w/w proportion of [protein]:[fiber]=1:0.7-2.4, setting [protein] weight as unity. In other embodiments, the w/w proportion of [protein]:[fiber]=1:0.8-2.3, setting [protein] weight as unity. In other embodiments, the w/w proportion of [protein]:[fiber]=1:0.9-2.2, setting [protein] weight as unity. In other embodiments, the w/w proportion of [protein]:[fiber]=1:0.9-2.1, setting [protein] weight as unity. In other embodiments, the w/w proportion of [protein]:[fiber]=1:0.9-2.0, setting [protein] weight as unity. In other embodiments, the w/w proportion of [protein]:[fiber]=1:0.9-1.9, setting [protein] weight as unity. In other embodiments, the w/w proportion of [protein]:[fiber]=1:0.9-1.8, setting [protein] weight as unity. In other embodiments, the w/w proportion of [protein]:[fiber]=1:0.9-1.7, setting [protein] weight as unity. In other embodiments, the w/w proportion of [protein]:[fiber]=1:0.9-1.6, setting [protein] weight as unity. In other embodiments, the w/w proportion of [protein]:[fiber]=1:0.9-1.5, setting [protein] weight as unity. In other embodiments, the w/w proportion of [protein]:[fiber]=1:0.9-1.4, setting [protein] weight as unity. In other embodiments, the w/w proportion of [protein]:[fiber]=1:0.9-1.3, setting [protein] weight as unity. In other embodiments, the w/w proportion of [protein]:[fiber]=1:0.9-1.2, setting [protein] weight as unity. In other embodiments, the w/w proportion of [protein]:[fiber]=1:0.9-1.1, setting [protein] weight as unity.

MPC is dairy protein. MPC can be in powder or liquid form. Green banana RS is green banana fiber. Maize RS is maize fiber. Oat beta glucan is oat fiber. Resistant dextrin is corn fiber. Each of green banana fiber, maize RS, oat beta glucan, and resistant dextrin include high amount of resistant starch that are health benefiting.

Green banana fiber includes significant amount of resistant starch. Such resistant starch sources have gelatinization temperatures that are typically on the order of about 60° C. to about 90° C. Green banana fiber includes more resistant starch than ripped banana.

Beta-D-glucans, usually referred to as beta glucans, comprise a class of fiber, indigestible polysaccharides found in nature in sources such as grains, barley, yeast, bacteria, algae and mushrooms. Beta-D-glucans includes high amount of prebiotic dietary fiber. Beta-D-glucans can be used in the embodiments of health benefiting daily nutritions disclosed herein. In oats, beta glucans are concentrated in the bran, more precisely in the aleurone and sub-aleurone layer. Oat beta glucan is a fiber with rich resistant starch. Oat beta glucan is richly stored in oat bran produced by removing the starchy content of the grain. Oat beta glucan is rich in dietary fibers, especially in soluble fibers, present in the inner periphery of the kernel. Oats contain more soluble fibers than any other grain, resulting in slower digestion and an extended sensation of fullness, among other things.

All of green banana fiber, maize fiber, oat fiber, and corn fiber include significant amount of resistant starch and prebiotic dietary fiber that are health benefiting. The health benefiting effects include improving bowel movements; reducing symptoms and promote regular bowel movements in those suffering constipation or irregular bowel symptoms; weight loss-often referred to as a second meal, resistant starch in this form allows you to eat once and have the satisfied feeling of eating twice. Fiber blend of this formulation also increases metabolism and removes aflatoxins and inflammation. Fiber blend of this formulation increases absorption and capacity of antioxidants and minerals—especially calcium which can aid in preventing osteoporosis. Fiber blend of this formulation promotes colon health and aide in the prevention of colon cancer. Fiber blend of this formulation prevents diabetes and aid in the treatment of diabetes. Fiber blend of this formulation lowers cholesterol and triglyceride levels. Fiber blend of this formulation reduces the incidence of gallstones and reduces symptoms of diarrhea.

In one method of use embodiment, the resistant starch included in this disclosure is mixed with water under the gelatinization temperature. In another method of use embodiment, the resistant starch included in this disclosure is mixed with water above the gelatinization temperature. In one method of production embodiment, it is possible to produce resistant starch by extensively processing, namely repeatedly cooking and cooling, starch pastes.

In example I, as shown in FIG. 1, fiber blend in w/w proportion of [green banana fiber]:[maize fiber]:[oat fiber]: [corn fiber]=1 (1.8-5.7 g):0.25-2.33 (1.4-4.2 g):0.35-3.33 (1.98-6 g):0.4-4.08 (2.25-7.35 g), setting green banana fiber as unity. In other embodiments, the fiber blend in w/w proportion of [green banana fiber]:[maize fiber]:[oat fiber]: [corn fiber]=1:0-5:0-5:0-5, setting green banana fiber as unity. In other embodiments, the fiber blend in w/w proportion of [green banana fiber]:[maize fiber]:[oat fiber]:[corn fiber]=1:0-4:0-4:0-4, setting green banana fiber as unity. In other embodiments, the fiber blend in w/w proportion of [green banana fiber]:[maize fiber]:[oat fiber]:[corn fiber]=1: 0-3:0-3:0-3, setting green banana fiber as unity. In other embodiments, the fiber blend in w/w proportion of [green banana fiber]:[maize fiber]:[oat fiber]:[corn fiber]=1:0-2:0-2:0-2, setting green banana fiber as unity. In yet other embodiments, the fiber blend in w/w proportion of [green banana fiber]:[maize fiber]:[oat fiber]:[corn fiber]=1:0.25-1.75:0.25-1.75:0.25-1.75, setting green banana fiber as unity. In yet other embodiments, the fiber blend in w/w proportion of [green banana fiber]:[maize fiber]:[oat fiber]: [corn fiber]=1:0.5-1.5:0.5-1.5:0.5-1.5, setting green banana fiber as unity. In yet other embodiments, the fiber blend in w/w proportion of [green banana fiber]:[maize fiber]:[oat fiber]:[corn fiber]=1:0.7-1.25:0.75-1.55:0.75-1.25, setting green banana fiber as unity. In yet other embodiments, the fiber blend in w/w proportion of [green banana fiber]:[maize fiber]:[oat fiber]:[corn fiber]=1:0.75-1.25:0.75-1.25:0.75-1.25, setting green banana fiber as unity. It is noted, the green banana fiber mentioned in the above formations can be replaced with beta-glucan soluble fiber, psyllium husk, cellulose, guar gum, pectin, locust bean gum, hydroxypropyl-methylcellulose, mixed plant cell wall fibers, arabinoxylan, alginate, inulin, high amylose resistant starch, galactooligo-saccharide, polydextrose, resistant maltodextrin, wheat fiber, rice fiber, pea fiber, barley fiber, triticale fiber, sorghum fiber, milo fiber, potato fiber/resistant starch, cassava fiber, sago fiber, sweet potato fiber, yam fiber, bean fiber, grain fiber, fruit fiber, root fiber, etc.

Sunflower oil powder is a form of fatty acids. Fatty acids included in the health benefiting daily nutrition disclosed herein also increases the sense of satisfaction, which reduces the overall intake of food for users. In another aspect, the composition comprises one or more of the following components: peanut oil, vegetable oil, avocado oil, olive oil, sunflower oil, safflower oil. In yet another aspect, the composition further comprises one or more of the following components: mustard oil, palm oil, soybean lecithin, almond oil, cashew oil, pumpkin seed oil, walnut oil, peanut oil, corn oil, olive oil, safflower oil, chia seed oil, cocoa oil, coconut oil, anhydrous butter oil, or the like.

Embodiments of using the health benefiting daily nutrition include a method of prophylaxis or treatment of a medical condition for a mammalian subject, said method comprising administering a therapeutically effective amount of the composition of any of the above embodiment to said subject, wherein said medical condition is linked with over-weight, immune system functionality, heart disease, blood sugar imbalance, diabetics, lipid imbalance in said mammalian subject. In one aspect, said medical condition is selected from the group consisting of: a symptom of menopause, a cardiovascular disease, a mental disorder, a neural disorder, a musculoskeletal disorder, an endocrine disorder, a cancer, a digestive system disorder, a symptom of aging, a viral infection, a bacterial infection, obesity, overweight, a renal disease, a pulmonary disorder, an ophthalmologic disorder, a dermatological disorder, a sleep disorder, a dental disease, an immune system disease, and an autoimmunity.

Vitamin mixture referred in this example is a powdery mixture of vitamins, including but not limited to VITAMIN A (Vitamin A Palmitate), VITAMIN D2 (Ergocalciferol), VITAMIN E (d,l-alpha Tocopheryl Acetate), VITAMIN K (Phytonadione), BIOTIN, THIAMIN (Thiamine Mononi-trate) RIBOFLAVIN, NIACIN (Niacinamide), PYRIDOX-INE (Pyridoxine Hydrochloride) PANTOTHENIC ACID (ct-Calcium Pantothenate) VITAMIN 8-12 (Cyanocobalamin), FOLATE (Folic Acid), CHOLINE (Choline Bitartrate), VITAMIN C (Ascorbic Acid), CHROMIUM (Chromium Picolinate), MAGNESIUM (Magnesium Oxide), CALCIUM (Calcium Carbonate), ZINC (Zinc Gluconate), IODINE (Potassium Iodide), IRON (Reduced Iron), COPPER (Copper Sulfate), MANGANESE (Manganese Sulfate) MOLYBDENUM (Sodium Molybdate) SELENIUM (Sodium Selenate), ALPHA LIPOIC ACID, Calcium Carbonate, Q.S. to 2,500.0 mg.

As shown in FIG. 1, Vanilla flavor mixture is flavor agent.

Reb M and allulose referred in FIG. 1 are non-glucose sweeteners. The thickening system including but not limited to, guar gum and xanthan gum, is included to increase the texture of the daily nutrition.

Example II. Formulation with Dairy Protein

The formulation of example II is shown in FIG. 2. The formulation includes (g): milk protein concentrate (MPC) 7.9-23.58, green banana RS (green banana fiber) 1.8-5.7, maize RS (maize fiber) 1.4-4.2, oat beta glucan (oat fiber) 1.98-6, and resistant dextrin (corn fiber) 2.25-6.7. The formulation also includes sunflower oil powder 2.45-7.35 (g). The weight of each item referred in this paragraph includes only active ingredient, not including the inactive impurities.

In example II, as shown in FIG. 2, fiber blend in w/w proportion of [green banana fiber]:[maize fiber]:[oat fiber]:[corn fiber]=1 (1.8-5.7 g):0.25-2.33 (1.4-4.2 g):0.35-3.33 (1.98-6 g):0.4-4.08 (2.25-7.35 g), setting green banana fiber as unity. In other embodiments, the fiber blend in w/w proportion of [green banana fiber]:[maize fiber]:[oat fiber]:[corn fiber]=1:0-5:0-5:0-5, setting green banana fiber as unity. In other embodiments, the fiber blend in w/w proportion of [green banana fiber]:[maize fiber]:[oat fiber]:[corn fiber]=1:0-4:0-4:0-4, setting green banana fiber as unity. In other embodiments, the fiber blend in w/w proportion of [green banana fiber]:[maize fiber]:[oat fiber]:[corn fiber]=1:0-3:0-3:0-3, setting green banana fiber as unity.

In one embodiment, the w/w proportions of the active ingredients in example II, as shown in FIG. 2, [protein]:[fiber]:[fat]=1:1:0.325, setting [protein] weight as unity.

In other embodiments, the w/w proportion of [protein]:[fiber]:[fat]=1:0.5-2.5:0.05-1, setting [protein] weight as unity. In other embodiments, the w/w proportion of [protein]:[fiber]:[fat]=1:0.6-2.4:0.1-0.9, setting [protein] weight as unity. In other embodiments, the w/w proportion of [protein]:[fiber]:[fat]=1:0.7-2.4:0.1-0.8, setting [protein] weight as unity. In other embodiments, the w/w proportion of [protein]:[fiber]:[fat]=1:0.8-2.3:0.1-0.7, setting [protein] weight as unity. In other embodiments, the w/w proportion of [protein]:[fiber]:[fat]=1:0.9-2.2:0.1-0.6, setting [protein] weight as unity. In other embodiments, the w/w proportion of [protein]:[fiber]:[fat]=1:0.9-2.1:0.1-0.5, setting [protein] weight as unity. In other embodiments, the w/w proportion of [protein]:[fiber]:[fat]=1:0.9-2.0:0.1-0.5, setting [protein] weight as unity. In other embodiments, the w/w proportion of [protein]:[fiber]:[fat]=1:0.9-1.9:0.1-0.4, setting [protein] weight as unity. In other embodiments, the w/w proportion of [protein]:[fiber]:[fat]=1:0.9-1.8:0.1-0.4, setting [protein] weight as unity. In other embodiments, the w/w proportion of [protein]:[fiber]:[fat]=1:0.9-1.7:0.1-0.4, setting [protein] weight as unity. In other embodiments, the w/w proportion of [protein]:[fiber]:[fat]=1:0.9-1.6:0.2-0.4, setting [protein] weight as unity. In other embodiments, the w/w proportion of [protein]:[fiber]:[fat]=1:0.9-1.5:0.2-0.4, setting [protein] weight as unity. In other embodiments, the w/w proportion of [protein]:[fiber]:[fat]=1:0.9-1.4:0.2-0.4, setting [protein] weight as unity. In other embodiments, the w/w proportion of [protein]:[fiber]:[fat]=1:0.9-1.3:0.2-0.4, setting [protein] weight as unity. In other embodiments, the w/w proportion of [protein]:[fiber]:[fat]=1:0.9-1.2:0.25-0.35, setting [protein] weight as unity. In other embodiments, the w/w proportion of [protein]:[fiber]:[fat]=1:0.9-1.1:0.25-0.35, setting [protein] weight as unity.

In other embodiments, [fat] can be omitted. In other embodiments, the w/w proportion of [protein]:[fiber]=1:0.5-2.5, setting [protein] weight as unity. In other embodiments, the w/w proportion of [protein]:[fiber]=1:0.6-2.4, setting [protein] weight as unity. In other embodiments, the w/w proportion of [protein]:[fiber]=1:0.7-2.4, setting [protein] weight as unity. In other embodiments, the w/w proportion of [protein]:[fiber]=1:0.8-2.3, setting [protein] weight as unity. In other embodiments, the w/w proportion of [protein]:[fiber]=1:0.9-2.2, setting [protein] weight as unity. In other embodiments, the w/w proportion of [protein]:[fiber]=1:0.9-2.1, setting [protein] weight as unity. In other embodiments, the w/w proportion of [protein]:[fiber]=1:0.9-2.0, setting [protein] weight as unity. In other embodiments, the w/w proportion of [protein]:[fiber]=1:0.9-1.9, setting [protein] weight as unity. In other embodiments, the w/w proportion of [protein]:[fiber]=1:0.9-1.8, setting [protein] weight as unity. In other embodiments, the w/w proportion of [protein]:[fiber]=1:0.9-1.7, setting [protein] weight as unity. In other embodiments, the w/w proportion of [protein]:[fiber]=1:0.9-1.6, setting [protein] weight as unity. In other embodiments, the w/w proportion of [protein]:[fiber]=1:0.9-1.5, setting [protein] weight as unity. In other embodiments, the w/w proportion of [protein]:[fiber]=1:0.9-1.4, setting [protein] weight as unity. In other embodiments, the w/w proportion of [protein]:[fiber]=1:0.9-1.3, setting [protein] weight as unity. In other embodiments, the w/w proportion of [protein]:[fiber]=1:0.9-1.2, setting [protein] weight as unity. In other embodiments, the w/w proportion of [protein]:[fiber]=1:0.9-1.1, setting [protein] weight as unity.

MPC is dairy protein. MPC can be in powder or liquid form. Green banana RS is green banana fiber. Maize RS is maize fiber. Oat beta glucan is oat fiber. Resistant dextrin is corn fiber. Each of green banana RS, maize RS, oat beta glucan, and resistant dextrin include high amount of prebiotic dietary fiber that are health benefiting.

Green banana fiber includes significant amount of resistant starch. Such resistant starch sources have gelatinization temperatures that are typically on the order of about 60° C. to about 90° C. Green banana fiber includes more resistant starch than ripped banana.

Beta-D-glucans, usually referred to as beta glucans, comprise a class of fiber, non-digestible polysaccharides found in nature in sources such as grains, barley, yeast, bacteria, algae and mushrooms. Beta-D-glucans includes high amount of prebiotic dietary fiber. Beta-D-glucans can be used in the embodiments of health benefiting daily nutrition disclosed herein. In oats, beta glucans are concentrated in the bran, more precisely in the aleurone and sub-aleurone layer. Oat beta glucan is richly stored in oat bran produced by removing the starchy content of the grain. Oat beta glucan is rich in dietary fibers, especially in soluble fibers, present in the inner periphery of the kernel. Oats contain more soluble fibers than any other grain, resulting in slower digestion and an extended sensation of fullness, among other things.

All green banana fiber, maize fiber, oat fiber, and corn fiber include significant amount of resistant starch and prebiotic dietary fiber that are health benefiting. The health benefiting effects include improving bowel movements; reducing symptoms and promote regular bowel movements in those suffering constipation or irregular bowel symptoms; weight loss-often referred to as a second meal, resistant starch in this form allows you to eat once and have the satisfied feeling of eating twice. Fiber blend of this formulation also increases metabolism and removes aflatoxins and inflammation. Fiber blend of this formulation increases absorption and capacity of antioxidants and minerals—especially calcium which can aid in preventing osteoporosis. Fiber blend of this formulation promotes colon health and aide in the prevention of colon cancer. Fiber blend of this formulation prevents diabetes and aid in the treatment of diabetes. Fiber blend of this formulation lowers cholesterol and triglyceride levels. Fiber blend of this formulation reduces the incidence of gallstones and reduces symptoms of diarrhea.

In one method of use embodiment, the resistant starch included in this disclosure is mixed with water under the gelatinization temperature. In another method of use embodiment, the resistant starch included in this disclosure is mixed with water above the gelatinization temperature. In one method of production embodiment, it is possible to produce resistant starch by extensively processing, namely repeatedly cooking and cooling, starch pastes.

In example II, as shown in FIG. 2, fiber blend in w/w proportion of [green banana fiber]:[maize fiber]:[oat fiber]: [corn fiber]=1 (1.8-5.7 g):0.25-2.33 (1.4-4.2 g):0.35-3.33 (1.98-6 g):0.4-4.08 (2.25-7.35 g), setting green banana fiber as unity. In other embodiments, the fiber blend in w/w proportion of [green banana fiber]:[maize fiber]:[oat fiber]: [corn fiber]=1:0-5:0-5:0-5, setting green banana fiber as unity. In other embodiments, the fiber blend in w/w proportion of [green banana fiber]:[maize fiber]:[oat fiber]:[corn fiber]=1:0-4:0-4:0-4, setting green banana fiber as unity. In other embodiments, the fiber blend in w/w proportion of [green banana fiber]:[maize fiber]:[oat fiber]:[corn fiber]=1: 0-3:0-3:0-3, setting green banana fiber as unity.

In other embodiments, the fiber blend in w/w proportion of [green banana fiber]:[maize fiber]:[oat fiber]:[corn fiber] =1:0-2:0-2:0-2, setting green banana fiber as unity. In yet other embodiments, the fiber blend in w/w proportion of [green banana fiber]:[maize fiber]:[oat fiber]:[corn fiber]=1: 0.25-1.75:0.25-1.75:0.25-1.75, setting green banana fiber as unity. In yet other embodiments, the fiber blend in w/w proportion of [green banana fiber]:[maize fiber]:[oat fiber]: [corn fiber]=1:0.5-1.5:0.5-1.5:0.5-1.5, setting green banana fiber as unity. In yet other embodiments, the fiber blend in w/w proportion of [green banana fiber]:[maize fiber]:[oat fiber]:[corn fiber]=1:0.7-1.25:0.75-1.55:0.75-1.25, setting green banana fiber as unity. In yet other embodiments, the fiber blend in w/w proportion of [green banana fiber]:[maize fiber]:[oat fiber]:[corn fiber]=1:0.75-1.25:0.75-1.25:0.75-1.25, setting green banana fiber as unity. It is noted, the green banana fiber mentioned in the above formations can be replaced with beta-glucan soluble fiber, psyllium husk, cellulose, guar gum, pectin, locust bean gum, hydroxypropylmethylcellulose, mixed plant cell wall fibers, arabinoxylan, alginate, inulin, high amylose resistant starch, galactooligosaccharide, polydextrose, resistant maltodextrin, wheat fiber, rice fiber, pea fiber, barley fiber, triticale fiber, sorghum fiber, milo fiber, potato fiber/resistant starch, cassava fiber, sago fiber, sweet potato fiber, yam fiber, bean fiber, grain fiber, fruit fiber, root fiber, etc.

Sunflower oil powder is a form of fatty acids. Fatty acids included in the health benefiting daily nutrition disclosed herein also increases the sense of satisfaction, which reduces the overall intake of food for users. In another aspect, the composition comprises one or more of the following components: peanut oil, vegetable oil, avocado oil, olive oil, sunflower oil, safflower oil. In yet another aspect, the composition further comprises one or more of the following components: mustard oil, palm oil, soybean lecithin, almond oil, cashew oil, pumpkin seed oil, walnut oil, peanut oil, corn oil, olive oil, safflower oil, chia seed oil, cocoa oil, coconut oil, anhydrous butter oil, or the like.

Embodiments of using the health benefiting daily nutrition include a method of prophylaxis or treatment of a medical condition for a mammalian subject, said method comprising administering a therapeutically effective amount of the composition of any of the above embodiment to said subject, wherein said medical condition is linked with overweight, immune system functionality, heart disease, blood sugar imbalance, diabetics, lipid imbalance in said mammalian subject. In one aspect, said medical condition is selected from the group consisting of: a symptom of menopause, a cardiovascular disease, a mental disorder, a neural disorder, a musculoskeletal disorder, an endocrine disorder, a cancer, a digestive system disorder, a symptom of aging, a viral infection, a bacterial infection, obesity, overweight, a renal disease, a pulmonary disorder, an ophthalmologic disorder, a dermatological disorder, a sleep disorder, a dental disease, an immune system disease, and an autoimmunity.

Vitamin mixture referred in this example is a powdery mixture of vitamins, including but not limited to VITAMIN A (Vitamin A Palmitate), VITAMIN D2 (Ergocalciferol), VITAMIN E (d,l-alpha Tocopheryl Acetate), VITAMIN K (Phytonadione), BIOTIN, THIAMIN (Thiamine Mononitrate) RIBOFLAVIN, NIACIN (Niacinamide), PYRIDOXINE (Pyridoxine Hydrochloride) PANTOTHENIC ACID (ct-Calcium Pantothenate) VITAMIN 8-12 (Cyanocobalamin), FOLATE (Folic Acid), CHOLINE (Choline Bitartrate), VITAMIN C (Ascorbic Acid), CHROMIUM (Chromium Picolinate), MAGNESIUM (Magnesium Oxide), CALCIUM (Calcium Carbonate), ZINC (Zinc Gluconate), IODINE (Potassium Iodide), IRON (Reduced Iron), COPPER (Copper Sulfate), MANGANESE (Manganese Sulfate) MOLYBDENUM (Sodium Molybdate) SELENIUM (Sodium Selenate), ALPHA LIPOIC ACID, Calcium Carbonate, Q.S. to 2,500.0 mg.

As shown in FIG. 2, NAT Chocolate and Cocoa Powder Sienna are flavor agents.

Reb M and allulose referred in FIG. 2 are non-glucose sweeteners. The thickening system including but not limited to guar gum and xanthan gum is included to increase the texture of the daily nutrition.

Example III. Formulation with Dairy Protein

The formulation of example III is shown in FIG. 3. The formulation includes (g): milk protein concentrate (MPC) 9.25-27.75, green banana RS (green banana fiber) 2.95-8.85, maize RS (maize fiber) 2.9-8.7, oat beta glucan (oat fiber) 2.6-7.9, and resistant dextrin (corn fiber) 2.5-7.5. The formulation also includes sunflower oil powder 3.5-10.5 (g). The weight of each item referred in this paragraph includes both active ingredient and impure non-active ingredient.

In example III, as shown in FIG. 3, fiber blend in w/w proportion of [green banana fiber]:[maize fiber]:[oat fiber]: [corn fiber]=1 (1.8-5.7 g):0.25-2.33 (1.4-4.2 g):0.35-3.33 (1.98-6 g):0.4-4.08 (2.25-7.35 g), setting green banana fiber as unity. In other embodiments, the fiber blend in w/w proportion of [green banana fiber]:[maize fiber]:[oat fiber]:

[corn fiber]=1:0-5:0-5:0-5, setting green banana fiber as unity. In other embodiments, the fiber blend in w/w proportion of [green banana fiber]:[maize fiber]:[oat fiber]:[corn fiber]=1:0-4:0-4:0-4, setting green banana fiber as unity. In other embodiments, the fiber blend in w/w proportion of [green banana fiber]:[maize fiber]:[oat fiber]:[corn fiber]=1: 0-3:0-3:0-3, setting green banana fiber as unity.

The w/w proportions of the active ingredients in example III, as shown in FIG. 3, [protein]:[fiber]:[fat]=1:1:0.325, setting [protein] weight as unity.

In one embodiment according to the disclosure, a health benefiting daily nutrition includes protein, fiber, and fat with a w/w ratio of 1:0.2-5:0-3, wherein each of the fiber and protein is more than 5 g. In one embodiment, the protein, fiber, and fat weight in (g) are 5-25:5-25:0-15. In other embodiments, the w/w proportion of [protein]:[fiber]:[fat] =1:0.6-2.4:0.1-0.9, setting [protein] weight as unity. In other embodiments, the w/w proportion of [protein]:[fiber]:[fat] =1:0.7-2.4:0.1-0.8, setting [protein] weight as unity. In other embodiments, the w/w proportion of [protein]:[fiber]:[fat] =1:0.8-2.3:0.1-0.7, setting [protein] weight as unity. In other embodiments, the w/w proportion of [protein]:[fiber]:[fat] =1:0.9-2.2:0.1-0.6, setting [protein] weight as unity. In other embodiments, the w/w proportion of [protein]:[fiber]:[fat] =1:0.9-2.1:0.1-0.5, setting [protein] weight as unity. In other embodiments, the w/w proportion of [protein]:[fiber]:[fat] =1:0.9-2.0:0.1-0.5, setting [protein] weight as unity. In other embodiments, the w/w proportion of [protein]:[fiber]:[fat] =1:0.9-1.9:0.1-0.4, setting [protein] weight as unity. In other embodiments, the w/w proportion of [protein]:[fiber]:[fat] =1:0.9-1.8:0.1-0.4, setting [protein] weight as unity. In other embodiments, the w/w proportion of [protein]:[fiber]:[fat] =1:0.9-1.7:0.1-0.4, setting [protein] weight as unity. In other embodiments, the w/w proportion of [protein]:[fiber]:[fat] =1:0.9-1.6:0.2-0.4, setting [protein] weight as unity. In other embodiments, the w/w proportion of [protein]:[fiber]:[fat] =1:0.9-1.5:0.2-0.4, setting [protein] weight as unity. In other embodiments, the w/w proportion of [protein]:[fiber]:[fat] =1:0.9-1.4:0.2-0.4, setting [protein] weight as unity. In other embodiments, the w/w proportion of [protein]:[fiber]:[fat] =1:0.9-1.3:0.2-0.4, setting [protein] weight as unity. In other embodiments, the w/w proportion of [protein]:[fiber]:[fat] =1:0.9-1.2:0.25-0.35, setting [protein] weight as unity. In other embodiments, the w/w proportion of [protein]:[fiber]: [fat]=1:0.9-1.1:0.25-0.35, setting [protein] weight as unity.

In other embodiments, [fat] can be omitted. In other embodiments, the w/w proportion of [protein]:[fiber]=1:0.5-2.5, setting [protein] weight as unity. In other embodiments, the w/w proportion of [protein]:[fiber]=1:0.6-2.4, setting [protein] weight as unity. In other embodiments, the w/w proportion of [protein]:[fiber]=1:0.7-2.4, setting [protein] weight as unity. In other embodiments, the w/w proportion of [protein]:[fiber]=1:0.8-2.3, setting [protein] weight as unity. In other embodiments, the w/w proportion of [protein]:[fiber]=1:0.9-2.2, setting [protein] weight as unity. In other embodiments, the w/w proportion of [protein]:[fiber]: =1:0.9-2.1, setting [protein] weight as unity. In other embodiments, the w/w proportion of [protein]:[fiber]=1:0.9-2.0, setting [protein] weight as unity. In other embodiments, the w/w proportion of [protein]:[fiber]=1:0.9-1.9, setting [protein] weight as unity. In other embodiments, the w/w proportion of [protein]:[fiber]=1:0.9-1.8, setting [protein] weight as unity. In other embodiments, the w/w proportion of [protein]:[fiber]=1:0.9-1.7, setting [protein] weight as unity. In other embodiments, the w/w proportion of [protein]:[fiber]=1:0.9-1.6, setting [protein] weight as unity. In other embodiments, the w/w proportion of [protein]:[fiber]

=1:0.9-1.5, setting [protein] weight as unity. In other embodiments, the w/w proportion of [protein]:[fiber]=1:0.9-1.4, setting [protein] weight as unity. In other embodiments, the w/w proportion of [protein]:[fiber]=1:0.9-1.3, setting [protein] weight as unity. In other embodiments, the w/w proportion of [protein]:[fiber]=1:0.9-1.2, setting [protein] weight as unity. In other embodiments, the w/w proportion of [protein]:[fiber]=1:0.9-1.1, setting [protein] weight as unity.

MPC is dairy protein. MPC can be in powder or liquid form. Green banana RS is green banana fiber. Maize RS is maize fiber. Oat beta glucan is oat fiber. Resistant dextrin is corn fiber. Each of Green banana fiber, maize RS, oat beta glucan, and resistant dextrin include high amount of resistant starch and prebiotic dietary fiber that are health benefiting.

Green banana fiber includes significant amount of resistant starch. Such resistant starch sources have gelatinization temperatures that are typically on the order of about 60° C. to about 90° C. Green banana fiber includes more resistant starch than ripped banana.

Beta-D-glucans, usually referred to as beta glucans, comprise a class of fiber, indigestible polysaccharides found in nature in sources such as grains, barley, yeast, bacteria, algae and mushrooms. Beta-D-glucans includes high amount of preniotic dietary fiber. Beta-D-glucans can be used in the embodiments of health benefiting daily nutritions disclosed herein. In oats, beta glucans are concentrated in the bran, more precisely in the aleurone and sub-aleurone layer. Oat beta glucan is richly stored in oat bran produced by removing the starchy content of the grain. Oat beta glucan is rich in dietary fibers, especially in soluble fibers, present in the inner periphery of the kernel. Oats contain more soluble fibers than any other grain, resulting in slower digestion and an extended sensation of fullness, among other things.

All of green banana fiber, maize fiber, oat fiber, and corn fiber include significant amount of resistant starch that are health benefiting. The health benefiting effects include improving bowel movements; reducing symptoms and promote regular bowel movements in those suffering constipation or irregular bowel symptoms; weight loss—often referred to as a second meal, resistant starch in this form allows you to eat once and have the satisfied feeling of eating twice. Fiber blend of this formulation also increases metabolism and removes aflatoxins and inflammation. Fiber blend of this formulation increases absorption and capacity of antioxidants and minerals—especially calcium which can aid in preventing osteoporosis. Fiber blend of this formulation promotes colon health and aide in the prevention of colon cancer. Fiber blend of this formulation prevents diabetes and aid in the treatment of diabetes. Fiber blend of this formulation lowers cholesterol and triglyceride levels. Fiber blend of this formulation reduces the incidence of gallstones and reduces symptoms of diarrhea.

In one method of use embodiment, the resistant starch included in this disclosure is mixed with water under the gelatinization temperature. In another method of use embodiment, the resistant starch included in this disclosure is mixed with water above the gelatinization temperature. In one method of production embodiment, it is possible to produce resistant starch by extensively processing, namely repeatedly cooking and cooling, starch pastes.

In example III, as shown in FIG. 3, fiber blend in w/w proportion of [green banana fiber]:[maize fiber]:[oat fiber]: [corn fiber]=1 (1.8-5.7 g):0.25-2.33 (1.4-4.2 g): 0.35-3.33 (1.98-6 g):0.4-4.08 (2.25-7.35 g), setting green banana fiber as unity. In other embodiments, the fiber blend in w/w proportion of [green banana fiber]:[maize fiber]:[oat fiber]: [corn fiber]=1:0-5:0-5:0-5, setting green banana fiber as unity. In other embodiments, the fiber blend in w/w proportion of [green banana fiber]:[maize fiber]:[oat fiber]:[corn fiber]=1:0-4:0-4:0-4, setting green banana fiber as unity. In other embodiments, the fiber blend in w/w proportion of [green banana fiber]:[maize fiber]:[oat fiber]:[corn fiber]=1:0-3:0-3:0-3, setting green banana fiber as unity.

In one embodiment according to the disclosure, a health benefiting daily nutrition includes protein, fiber, and fat with a w/w ratio of 1:0.2-5:0-3, wherein each of the fiber and protein is more than 5 g. In one embodiment, the protein, fiber, and fat weight in (g) are 5-25:5-25:0-15.

In other embodiments, the fiber blend in w/w proportion of [green banana fiber]:[maize fiber]:[oat fiber]:[corn fiber]=1:0-2:0-2:0-2, setting green banana fiber as unity. In yet other embodiments, the fiber blend in w/w proportion of [green banana fiber]:[maize fiber]:[oat fiber]:[corn fiber]=1:0.25-1.75:0.25-1.75:0.25-1.75, setting green banana fiber as unity. In yet other embodiments, the fiber blend in w/w proportion of [green banana fiber]:[maize fiber]:[oat fiber]:[corn fiber]=1:0.5-1.5:0.5-1.5:0.5-1.5, setting green banana fiber as unity. In yet other embodiments, the fiber blend in w/w proportion of [green banana fiber]:[maize fiber]:[oat fiber]:[corn fiber]=1:0.7-1.25:0.75-1.55:0.75-1.25, setting green banana fiber as unity. In yet other embodiments, the fiber blend in w/w proportion of [green banana fiber]:[maize fiber]:[oat fiber]:[corn fiber]=1:0.75-1.25:0.75-1.25:0.75-1.25, setting green banana fiber as unity. It is noted, the green banana fiber mentioned in the above formations can be replaced with beta-glucan soluble fiber, psyllium husk, cellulose, guar gum, pectin, locust bean gum, hydroxypropylmethylcellulose, mixed plant cell wall fibers, arabinoxylan, alginate, inulin, RS2-high amylose starch, galactooligosaccharide, polydextrose, resistant maltodextrin, wheat fiber, rice fiber, pea fiber, barley fiber, triticale fiber, sorghum fiber, milo fiber, potato fiber, cassava fiber, sago fiber, sweet potato fiber, yam fiber, bean fiber, grain fiber, fruit fiber, root fiber, etc.

Sunflower oil powder is a form of fatty acids. Fatty acids included in the health benefiting daily nutrition disclosed herein also increases the sense of satisfaction, which reduces the overall intake of food for users. In another aspect, the composition comprises one or more of the following components: peanut oil, vegetable oil, avocado oil, olive oil, sunflower oil, safflower oil. In yet another aspect, the composition further comprises one or more of the following components: mustard oil, palm oil, soybean lecithin, almond oil, cashew oil, pumpkin seed oil, walnut oil, peanut oil, corn oil, olive oil, safflower oil, chia seed oil, cocoa oil, coconut oil, anhydrous butter oil, or the like.

Embodiments of using the health benefiting daily nutrition include a method of prophylaxis or treatment of a medical condition for a mammalian subject, said method comprising administering a therapeutically effective amount of the composition of any of the above embodiment to said subject, wherein said medical condition is linked with overweight, immune system functionality, heart disease, blood sugar imbalance, diabetics, lipid imbalance in said mammalian subject. In one aspect, said medical condition is selected from the group consisting of: a symptom of menopause, a cardiovascular disease, a mental disorder, a neural disorder, a musculoskeletal disorder, an endocrine disorder, a cancer, a digestive system disorder, a symptom of aging, a viral infection, a bacterial infection, obesity, overweight, a renal disease, a pulmonary disorder, an ophthalmologic disorder, a dermatological disorder, a sleep disorder, a dental disease, an immune system disease, and an autoimmunity.

Vitamin mixture referred in this example is a powdery mixture of vitamins, including but not limited to VITAMIN A (Vitamin A Palmitate), VITAMIN D2 (Ergocalciferol), VITAMIN E (d, 1-alpha Tocopheryl Acetate), VITAMIN K (Phytonadione), BIOTIN, THIAMIN (Thiamine Mononitrate) RIBOFLAVIN, NIACIN (Niacinamide), PYRIDOXINE (Pyridoxine Hydrochloride) PANTOTHENIC ACID (ct-Calcium Pantothenate) VITAMIN 8-12 (Cyanocobalamin), FOLATE (Folic Acid), CHOLINE (Choline Bitartrate), VITAMIN C (Ascorbic Acid), CHROMIUM (Chromium Picolinate), MAGNESIUM (Magnesium Oxide), CALCIUM (Calcium Carbonate), ZINC (Zinc Gluconate), IODINE (Potassium Iodide), IRON (Reduced Iron), COPPER (Copper Sulfate), MANGANESE (Manganese Sulfate) MOLYBDENUM (Sodium Molybdate) SELENIUM (Sodium Selenate), ALPHA LIPOIC ACID, Calcium Carbonate, Q.S. to 2,500.0 mg.

As shown in FIG. 3, Mocha Flavor, NAT Chocolate, Cocoa Powder Sienna, and Coffee Dark Roast are flavor agents.

Reb M and allulose referred in FIG. 3 are non-glucose sweeteners. Anti-foaming agent is included to increase the texture of the daily nutrition. Thickening agent, e.g., Xanthan gum, and/or Guar Gum, is included in the formulation to improve the texture.

Example IV. Formulation with Vegan Protein

The formulation of example IV is shown in FIG. 4. The formulation includes (g): non-animal protein 5-25, green banana RS (green banana fiber) 3-7, maize RS (maize fiber) 3-7, oat beta glucan (oat fiber) 3-7, and resistant dextrin (corn fiber) 3-7. The formulation also includes sunflower oil powder 5-9 (g). In one embodiment, the non-animal protein blend may include in (g): pea protein 10-20, rice protein 1-3, pumpkin seed protein 1-5. The weight of each item referred in this paragraph includes both active ingredient and impure non-active ingredient.

Calculating the active ingredients (considering the purity), the formulation of this example includes (g): non-animal protein 4-20, green banana RS (green banana fiber) 1.92-4.48, maize RS (maize fiber) 1.45-3.38, oat beta glucan (oat fiber) 2.28-5.33, and resistant dextrin (corn fiber) 2.7-6.3. The formulation also includes active sunflower oil powder 3.5-6.3 (g).

In example IV, as shown in FIG. 4, fiber blend in w/w proportion of [green banana fiber]:[maize fiber]:[oat fiber]:[corn fiber]=1 (1.92-4.48 g):0.32-1.76 (1.45-3.38 g):0.51-2.78 (2.28-5.33 g):0.6-3.28 (2.7-6.3 g), setting green banana fiber as unity. In other embodiments, the fiber blend in w/w proportion of [green banana fiber]:[maize fiber]:[oat fiber]:[corn fiber]=1:0-5:0-5:0-5, setting green banana fiber as unity. In other embodiments, the fiber blend in w/w proportion of [green banana fiber]:[maize fiber]:[oat fiber]:[corn fiber]=1:0-4:0-4:0-4, setting green banana fiber as unity. In other embodiments, the fiber blend in w/w proportion of [green banana fiber]:[maize fiber]:[oat fiber]:[corn fiber]=1:0-3:0-3:0-3, setting green banana fiber as unity.

In one embodiment according to the disclosure, a health benefiting daily nutrition includes protein, fiber, and fat with a w/w ratio of 1:0.2-5:0-3, wherein each of the fiber and protein is more than 5 g. In one embodiment, the protein, fiber, and fat weight in (g) are 5-25:5-25:0-15.

In other embodiments, the w/w proportion of [protein]:[fiber]:[fat]=1:0.5-2.5:0-1, setting [protein] weight as unity.

In other embodiments, the w/w proportion of [protein]:[fiber]:[fat]=1:0.6-2.4:0.1-0.9, setting [protein] weight as unity. In other embodiments, the w/w proportion of [protein]:[fiber]:[fat]=1:0.7-2.4:0.1-0.8, setting [protein] weight as unity. In other embodiments, the w/w proportion of [protein]:[fiber]:[fat]=1:0.8-2.3:0.1-0.7, setting [protein] weight as unity. In other embodiments, the w/w proportion of [protein]:[fiber]:[fat]=1:0.9-2.2:0.1-0.6, setting [protein] weight as unity. In other embodiments, the w/w proportion of [protein]:[fiber]:[fat]=1:0.9-2.1:0.1-0.5, setting [protein] weight as unity. In other embodiments, the w/w proportion of [protein]:[fiber]:[fat]=1:0.9-2.0:0.1-0.5, setting [protein] weight as unity. In other embodiments, the w/w proportion of [protein]:[fiber]:[fat]=1:0.9-1.9:0.1-0.4, setting [protein] weight as unity. In other embodiments, the w/w proportion of [protein]:[fiber]:[fat]=1:0.9-1.8:0.1-0.4, setting [protein] weight as unity. In other embodiments, the w/w proportion of [protein]:[fiber]:[fat]=1:0.9-1.7:0.1-0.4, setting [protein] weight as unity. In other embodiments, the w/w proportion of [protein]:[fiber]:[fat]=1:0.9-1.6:0.2-0.4, setting [protein] weight as unity. In other embodiments, the w/w proportion of [protein]:[fiber]:[fat]=1:0.9-1.5:0.2-0.4, setting [protein] weight as unity. In other embodiments, the w/w proportion of [protein]:[fiber]:[fat]=1:0.9-1.4:0.2-0.4, setting [protein] weight as unity. In other embodiments, the w/w proportion of [protein]:[fiber]:[fat]=1:0.9-1.3:0.2-0.4, setting [protein] weight as unity. In other embodiments, the w/w proportion of [protein]:[fiber]:[fat]=1:0.9-1.2:0.25-0.4, setting [protein] weight as unity. In other embodiments, the w/w proportion of [protein]:[fiber]:[fat]=1:0.9-1.1:0.3-0.4, setting [protein] weight as unity.

In other embodiments, [fat] can be omitted. In other embodiments, the w/w proportion of [protein]:[fiber]=1:0.5-2.5, setting [protein] weight as unity. In other embodiments, the w/w proportion of [protein]:[fiber]=1:0.6-2.4, setting [protein] weight as unity. In other embodiments, the w/w proportion of [protein]:[fiber]=1:0.7-2.4, setting [protein] weight as unity. In other embodiments, the w/w proportion of [protein]:[fiber]=1:0.8-2.3, setting [protein] weight as unity. In other embodiments, the w/w proportion of [protein]:[fiber]=1:0.9-2.2, setting [protein] weight as unity. In other embodiments, the w/w proportion of [protein]:[fiber]=1:0.9-2.1, setting [protein] weight as unity. In other embodiments, the w/w proportion of [protein]:[fiber]=1:0.9-2.0, setting [protein] weight as unity. In other embodiments, the w/w proportion of [protein]:[fiber]=1:0.9-1.9, setting [protein] weight as unity. In other embodiments, the w/w proportion of [protein]:[fiber]=1:0.9-1.8, setting [protein] weight as unity. In other embodiments, the w/w proportion of [protein]:[fiber]=1:0.9-1.7, setting [protein] weight as unity. In other embodiments, the w/w proportion of [protein]:[fiber]=1:0.9-1.6, setting [protein] weight as unity. In other embodiments, the w/w proportion of [protein]:[fiber]=1:0.9-1.5, setting [protein] weight as unity. In other embodiments, the w/w proportion of [protein]:[fiber]=1:0.9-1.4, setting [protein] weight as unity. In other embodiments, the w/w proportion of [protein]:[fiber]=1:0.9-1.3, setting [protein] weight as unity. In other embodiments, the w/w proportion of [protein]:[fiber]=1:0.9-1.2, setting [protein] weight as unity. In other embodiments, the w/w proportion of [protein]:[fiber]=1:0.9-1.1, setting [protein] weight as unity.

Green banana RS is green banana fiber. Maize RS is maize fiber. Oat beta glucan is oat fiber. Resistant dextrin is corn fiber. Each of green banana RS, maize RS, oat beta glucan, and resistant dextrin include high amount of prebiotic dietary fibers that are health benefiting.

Green banana fiber includes significant amount of resistant starch. Such resistant starch sources have gelatinization temperatures that are typically on the order of about 60° C. to about 90° C. Green banana fiber includes more resistant starch than ripped banana.

Beta-D-glucans, usually referred to as beta glucans, comprise a class of fiber, indigestible polysaccharides found in nature in sources such as grains, barley, yeast, bacteria, algae and mushrooms. Beta-D-glucans includes high amount of prebiotic dietary fiber. Beta-D-glucans can be used in the embodiments of health benefiting daily nutritions disclosed herein. In oats, beta glucans are concentrated in the bran, more precisely in the aleurone and sub-aleurone layer. Oat beta glucan is richly stored in oat bran produced by removing the starchy content of the grain. Oat beta glucan is rich in dietary fibers, especially in soluble fibers, present in the inner periphery of the kernel. Oats contain more soluble fibers than any other grain, resulting in slower digestion and an extended sensation of fullness, among other things.

All of green banana fiber, maize fiber, oat fiber, and corn fiber include significant amount of prebiotic dietary fibers that are health benefiting. The health benefiting effects include improving bowel movements; reducing symptoms and promote regular bowel movements in those suffering constipation or irregular bowel symptoms; weight loss—often referred to as a second meal, resistant starch in this form allows you to eat once and have the satisfied feeling of eating twice. Fiber blend of this formulation also increases metabolism and removes aflatoxins and inflammation. Fiber blend of this formulation increases absorption and capacity of antioxidants and minerals—especially calcium which can aid in preventing osteoporosis. Fiber blend of this formulation promotes colon health and aide in the prevention of colon cancer. Fiber blend of this formulation prevents diabetes and aid in the treatment of diabetes. Fiber blend of this formulation lowers cholesterol and triglyceride levels. Fiber blend of this formulation reduces the incidence of gallstones and reduces symptoms of diarrhea.

In one method of use embodiment, the resistant starch included in this disclosure is mixed with water under the gelatinization temperature. In another method of use embodiment, the resistant starch included in this disclosure is mixed with water above the gelatinization temperature. In one method of production embodiment, it is possible to produce resistant starch by extensively processing, namely repeatedly cooking and cooling, starch pastes.

In example IV, as shown in FIG. 4, fiber blend in w/w proportion of [green banana fiber]:[maize fiber]:[oat fiber]:[corn fiber]=1 (1.92-4.48 g):0.32-1.76 (1.45-3.38 g): 0.51-2.78 (2.28-5.33 g):0.6-3.28 (2.7-6.3 g), setting green banana fiber as unity. In other embodiments, the fiber blend in w/w proportion of [green banana fiber]:[maize fiber]:[oat fiber]:[corn fiber]=1:0-5:0-5:0-5, setting green banana fiber as unity. In other embodiments, the fiber blend in w/w proportion of [green banana fiber]:[maize fiber]:[oat fiber]:[corn fiber]=1:0-4:0-4:0-4, setting green banana fiber as unity. In other embodiments, the fiber blend in w/w proportion of [green banana fiber]:[maize fiber]:[oat fiber]:[corn fiber]=1:0-3:0-3:0-3, setting green banana fiber as unity. In other embodiments, the fiber blend in w/w proportion of [green banana fiber]:[maize fiber]:[oat fiber]:[corn fiber]=1:0-2:0-2:0-2, setting green banana fiber as unity. In yet other embodiments, the fiber blend in w/w proportion of [green banana fiber]:[maize fiber]:[oat fiber]:[corn fiber]=1:0.25-1.75:0.25-1.75:0.25-1.75, setting green banana fiber as unity. In yet other embodiments, the fiber blend in w/w proportion of [green banana fiber]:[maize fiber]:[oat fiber]:

[corn fiber]=1:0.5-1.5:0.5-1.5:0.5-1.5, setting green banana fiber as unity. In yet other embodiments, the fiber blend in w/w proportion of [green banana fiber]:[maize fiber]:[oat fiber]:[corn fiber]=1:0.7-1.25:0.75-1.55:0.75-1.25, setting green banana fiber as unity. In yet other embodiments, the fiber blend in w/w proportion of [green banana fiber]:[maize fiber]:[oat fiber]:[corn fiber]=1:0.75-1.25:0.75-1.25:0.75-1.25, setting green banana fiber as unity. It is noted, the green banana fiber mentioned in the above formations can be replaced with beta-glucan soluble fiber, psyllium husk, cellulose, guar gum, pectin, locust bean gum, hydroxypropyl-methylcellulose, mixed plant cell wall fibers, arabinoxylan, alginate, inulin, high amylose resistant starch, galactooligo-saccharide, polydextrose, resistant maltodextrin, wheat fiber, rice fiber, pea fiber, barley fiber, triticale fiber, sorghum fiber, milo fiber, potato fiber, cassava fiber, sago fiber, sweet potato fiber, yam fiber, bean fiber, grain fiber, fruit fiber, root fiber, etc.

Sunflower oil powder is a form of fatty acids. Fatty acids included in the health benefiting daily nutrition disclosed herein also increases the sense of satisfaction, which reduces the overall intake of food for users. In another aspect, the composition comprises one or more of the following components: peanut oil, vegetable oil, avocado oil, olive oil, sunflower oil, safflower oil. In yet another aspect, the composition further comprises one or more of the following components: mustard oil, palm oil, soybean lecithin, almond oil, cashew oil, pumpkin seed oil, walnut oil, peanut oil, corn oil, olive oil, safflower oil, chia seed oil, cocoa oil, coconut oil, anhydrous butter oil, or the like.

Embodiments of using the health benefiting daily nutrition include a method of prophylaxis or treatment of a medical condition for a mammalian subject, said method comprising administering a therapeutically effective amount of the composition of any of the above embodiment to said subject, wherein said medical condition is linked with over-weight, immune system functionality, heart disease, blood sugar imbalance, diabetics, lipid imbalance in said mammalian subject. In one aspect, said medical condition is selected from the group consisting of: a symptom of menopause, a cardiovascular disease, a mental disorder, a neural disorder, a musculoskeletal disorder, an endocrine disorder, a cancer, a digestive system disorder, a symptom of aging, a viral infection, a bacterial infection, obesity, overweight, a renal disease, a pulmonary disorder, an ophthalmologic disorder, a dermatological disorder, a sleep disorder, a dental disease, an immune system disease, and an autoimmunity.

Vitamin mixture referred in this example is a powdery mixture of vitamins, including but not limited to VITAMIN A (Vitamin A Palmitate), VITAMIN D2 (Ergocalciferol), VITAMIN E (d, 1-alpha Tocopheryl Acetate), VITAMIN K (Phytonadione), BIOTIN, THIAMIN (Thiamine Mononi-trate) RIBOFLAVIN, NIACIN (Niacinamide), PYRIDOX-INE (Pyridoxine Hydrochloride) PANTOTHENIC ACID (ct-Calcium Pantothenate) VITAMIN 8-12 (Cyanocobala-min), FOLATE (Folic Acid), CHOLINE (Choline Bitar-trate), VITAMIN C (Ascorbic Acid), CHROMIUM (Chro-mium Picolinate), MAGNESIUM (Magnesium Oxide), CALCIUM (Calcium Carbonate), ZINC (Zinc Gluconate), IODINE (Potassium Iodide), IRON (Reduced Iron), COP-PER (Copper Sulfate), MANGANESE (Manganese Sulfate) MOLYBDENUM (Sodium Molybdate) SELENIUM (So-dium Selenate), ALPHA LIPOIC ACID, Calcium Carbon-ate, Q.S. to 2,500.0 mg.

As shown in FIG. 4, NAT Chocolate and Cocoa Powder Sienna are flavor agents.

Reb M and allulose referred in FIG. 4 are non-glucose sweeteners. Anti-foaming agent is included to increase the texture of the daily nutrition. Thickening agent, e.g., Xanthan gum, and/or Guar Gum, is included in the formulation to improve the texture.

Example V. Methods of Processing

Blending, pressing, rolling, pealing, crushing, cooking, heating, cooling, adding water, or other processing of resistant starch source, e.g., green banana, corn, maize, oat, wheat, rice, barley, seeds, beans, etc may affect the resistant starch content of the processed foods. In some embodiments, the processing may increase the resistant starch contents. For example, rolling, pressing, crushing, or pealing whole grains of wheat, barley, oat, rice, corn kernel, maize kernel, or the like can increase the resistant starch, because those processes break down the physical barriers and release the resistant starches that are naturally aggregated in particulates in those grains.

In other embodiments, the processing may reduce the resistant starch contents. For example, blending, cooking, milling, may shorten the chemical chains of resistant starches making them easier to digest, resulting in a reduc-tion of resistant starches. Whole grain wheat may contain as high as 14% resistant starch, while milled wheat flour may contain only 2%. Resistant starch content of cooked rice may decrease due to grinding or cooking.

In other embodiments, cooling of cooked resistant starch food source may increase the resistant starch amount. For example, cooling of a cooked oat meal, or rice, or pasta, etc increases the resistant starch amount, because resistant starches broken down due to the process of cooking may recombine with each other in the cooling process.

In other examples, if cooking includes excess water, the starch is gelatinized and becomes more digestible which loses the resistant starch. However, if these starch gels are then cooled, they can form starch crystals resistant to digestive enzymes, such as those occurring in cooked and cooled cereals or potatoes (e.g., potato salad). Cooling a boiled potato overnight increases the amount of resistant starch.

Green banana flour, 1 cup uncooked, may include 42-52 g of resistant starch. Raw banana (slightly green), medium size, peel, may include 4.7 g resistant starch. High amylose corn resistant starch, 1 tablespoon (9.5 g), may include 4.7 g resistant starch. Oats, rolled, 1 cup, uncooked, may include 17.6 g of resistant starch. Green peas, 1 cup, cooked, may include 4 g of resistant starch. White beans, 1 cup, cooked, may include 7.4 g of resistant starch. Lentils, 1 cup cooded, may include 5 g of resistant starch. Cold pasta, 1 cup, may include 1.9 g of resistant starch. Barley, 1 cup cooked, may include 3.2 g of resistant starch. Potato, medium size, may include 0.6-0.8 g of resistant starch. Oatmeal, 1 cup cooked, may include 0.5 g of resistant starch.

Example VI. Protein

In some embodiments, the health benefiting daily nutri-tions may include dairy protein, such as milk protein con-centrate (isolate), whey protein concentrate (isolate), casein and caseinate, milk or dairy powders, hydrolysates, dairy protein, etc.

In other embodiments, the health benefiting daily nutri-tions may include vegan protein, such as pea protein; rice protein; pumpkin seed protein; mung bean protein; fava bean protein (aka broad or faba); oat protein; potato protein;

soy protein; chickpea protein; wheat protein; hemp protein; cranberry seed protein; spirulina protein; chlorella protein; chia protein; watergrass protein; yeast protein; rapeseed/ canola protein; mushroom protein; sacha inchi; duckweed; carob; lentil; coix seed; alfalfa; sunflower seed; almond; lupine; coconut; pomegranate; artichoke; seabuckthorn; spelt; quinoa; degreened lentein, etc.

Example VII. Fiber

In some embodiments, the health benefiting daily nutritions may include fiber from beta-glucan soluble fiber, psyllium husk, cellulose, guar gum, pectin, locust bean gum, hydroxypropylmethylcellulose, mixed plant cell wall fibers, Arabinoxylan, Alginate, Inulin, RS2-High Amylose Starch, Galactooligosaccharide, Polydextrose, Resistant Maltodextrin, etc.

Example VIII. Clinical Data for Blood Sugar Control

FIG. 5 and FIG. 6 show blood sugar testing data of the subjects using the health benefiting daily nutritions disclosed herein according to one embodiment of the disclosure. FIG. shows the statistical data from the test subjects shown in FIG. 6.

Study Brief

Over the course of 3 weeks, a group of 21 people were asked to consume 1 serving/meal of the a health benefiting daily nutrition disclosed in Example I, II, III, and IV (randomly) with their regular diet on a daily basis and log their blood sugar results along the way. The group was diverse in terms of gender, age, race as well health condition (non-diabetic, pre-diabetic, diabetic). The first set of data-points ("day 0" in FIG. 5) is collected before they start using the health benefiting daily nutrition disclosed herein and reflects their blood sugar results related to their regular breakfast. The other blood sugar measurements were taken on days 7, 14 and 21 and people were asked to consume the health benefiting daily nutrition (powder, water and ice only) in the morning fasted. On each of these days, people took their blood sugar results right before breakfast, as well as 30 mins, 60 mins and 120 mins after finishing their shake.

Data and Methods

Subjects shown in FIG. 6 were requested to test blood sugar at day 0, 7, 14, and 21. Raw data were reviewed and analyzed. All the data was entered into Student's T-test calculator for P value calculation against to Day 0 data set. Data set of each time point (0, 30, 60, and 120 minutes) on each day (7, 14, and 21) was compared to each time point on day 0, respectively. The T-test is a simple and one-tailed. Furthermore, the average of each time point on day 7, 14, and 21 were calculated and p value of these averages were calculated against day 0. The statistical results are shown in FIG. 5.

Results

As shown in FIG. 5, based on the blood sugar data, T-60 data point on day 14 is significant different from day 0 when P value is <0.05. However, T-60 data point on day 7 and 21 are significant different from day 0 when P value is <0.1. The average data suggests that only T-60 is significant different from day 0 ($P < 0.05$).

Example IX. Methods to Process, Create, Purify, Concentrate Resistant Starches from Natural Food Sources Resistant Starch (RS) can be prepared by using heat treatment, enzyme treatment, combined heat treatment and enzyme treatment, and chemical treatment. In this disclosure, all the methods disclosed below can be used in all suitable resistant starch food sources disclosed in various embodiments.

Heat Treatment

Heat treatment of starch to various extents leads to formation of RS. RS can be obtained by cooking the starch above the gelatinization temperature and simultaneously drying on heated rolls like drum driers or even extruders. The gelatinization of starch granules by heat processing strongly influences their susceptibility to enzymatic hydrolysis. In a high-moisture environment, amylose leaches from the granules, increasing the solubility of starch and thereby its susceptibility to enzyme hydrolysis.

The moisture control while heat treating the RS food source can influence the yield of RS. Good yields of RS can be obtained by gelatinizing starch at 100-120° C. for 10-40 min, with 10-30 W % water, followed by cooling to room temperature. Further, the starch gels can then be frozen overnight at −5 to −20° C. and dried at 60° C. before milling.

Many combinations of time and temperature treatments can be used to produce type III RS (recrystallized RS after heat and moisture controlled treatment) from various raw food sources. Even for starches with normal amylose levels, it is recognized that cooking at >100° C. can increase the yield of type III RS. In one embodiment, the temperature treatments have included autoclaving the starch at 110-150° C., for periods ranging from 5 min to 2 h.

A type III RS, which has a melting point or endothermic peak of at least about 140° C., as determined by differential scanning calorimetry (DSC) can be produced in yields of at least 25% by weight, based on the weight of the original starch ingredient.

In one embodiment, a raw food source is heated to its gelatinization point, aka gelatinization stage. In some embodiments, it is followed with nucleation/propagation stage, and preferably a heat-treatment stage to produce reduced calorie starch-based compositions that contain the enzyme-resistant starch. Such RS is produced using crystal nucleation and propagation temperatures, which avoid substantial production of lower melting amylopectin crystals, lower melting amylose crystals, and lower melting amylose-lipid complexes. The nucleating temperature used is higher than the melting point of the RS. The propagating temperature used is higher than the melting point of any amylose-lipid complexes but lower than the melting point of the RS. The high melting point of the enzyme RS permits its use in baked good formulations.

Heat with acid. Partial acid hydrolysis (PAH) of a high-amylose food source, e.g., corn starch, enhances the effects of hydrothermal treatments used to produce granular RS, which is stable to further heat treatment at atmospheric pressure. PAH of food starch may involve heating 35% (w/v) starch suspensions with 1% (w/w) HCl at 25° C. for up to 78 h. PAH followed by heat moisture treatment tended to increase yield of boiling-stable granular RS to the maximum of 63.2%.

Heat treat with swelling inhibitor. Selective heat treatment of high amylose starch in the presence of agents inhibiting the swelling of starch like alkali and alkaline earth metal salts of halides, sulfates, and phosphates yield granular RS with high dietary fiber.

Dry heat. Dry heat caused pyrodextrinization can produce RS from natural food source that is water-soluble and has non-starch linkages. Pyroconversion refers strictly to the modification of dry starch through heat treatments, with or without addition of acids. Acids used include hydrochloric acid at 0.15 W % (based on starch dry weight) and ortho-phosphoric or sulfuric acids at 0.17%. Commercial pyro-dextrins are generally produced by heating dry, acidified starch in a reactor with agitation. Acid may be sprayed on the starch to facilitate hydrolysis and transglycosidation. Depending on reaction conditions, pyroconversion produces a range of products that vary in digestibility, available starch, viscosity, cold-water solubility, swelling power, color, and stability. The production of indigestible dextrins or pyro-dextrins by heat-treating potato starch in the presence of an acid and then refining the product has been described.

Enzyme Treatment

By use of a thermally stable amylose cutting enzyme, e.g., □-amylase, a preparation of up to 70% RS containing a mixture of mineral and organic N compounds was obtained. In one embodiment, the pea RS concentrate had an affinity to bile acid, deoxycholic, and cholesterol. In some embodi-ment, pea RS concentrate may be potentially used as a food component in special diets, or for preventive, prophylactic, and therapeutic purposes.

Readily fermentable heat-stable RS of optimal chain length from poly-1,4-□-D-glucan useful in various func-tional foods can be obtained by in vitro synthesis by adding an enzyme extract containing the amylosucrase of Neisseria polysaccharea to sucrose solutions, followed by incubation at 37° C. over several hours.

In one embodiment, a method has been used to produce an RS product that retains the same cooking quality as found in untreated rice starch or flour, but has a higher percentage of starch resistant to □-amylase digestion. This method may use a debranching enzyme, that is, pullulanase, to digest the starch, but does not require pretreating the starch source before enzymatic treatment. This method produced RS from low amylose starches, rice starch (24%), and rice flour (20%). Surprisingly the RS product formed by this method retained the pasting characteristics of the untreated flour or starch and was heat stable. This method may also be used to produce RS from other botanical sources, e.g., corn, wheat, potato, oat, barley, tapioca, sago, and arrowroot.

Heat and Enzyme Treatment

Preparation of RS to be used as a food-grade bulking agent, by retrogradation of starch followed by enzymatic or chemical hydrolysis to reduce or remove the amorphous regions of retrograded starch. RS can be prepared from high amylose starch by gelatinization followed by treating the slurry with debranching enzymes like pullulanase and iso-lating the starch product by drying/extrusion. Controlled heat treatment of starch so as to achieve swelling and at the same time retain its granular structure followed by enzy-matic debranching and annealing at suitable temperature followed by drying produces RS. These RS find applications in a variety of foods and beverage products.

Purified RS products having at least 50% RS content can be produced by forming a water-starch mixture wherein the ratio of starch to water is approximately 1:2 to 1:20, heating the water-starch mixture in an autoclave at temperatures above 100° C. to ensure full starch gelatinization and then cooling to allow amylose retrogradation to take place. In one embodiment, the best results were obtained at a temperature of 134° C., with 4 heating and cooling cycles and a starch: water ratio of 1:3.5. The RS was purified by comminuting the starch gel and mixing it with an amylase to digest non-RS fractions, leaving RS. The amylase is inactivated by heat treatment above 100° C.

In one embodiment, for the preparation of a fragmented starch precipitate for use in reduced-fat foods, a debranched amylopectin starch is precipitated and then fragmented. The debranched amylopectin starch may be derived from a starch that contains amylopectin, for example, common corn starch and waxy maize starch, by gelatinizing the starch, followed by treatment with a debranching enzyme, such as isoamy-lase or pullulanase, and precipitation of the debranched starch. To form the precipitate, the solution is cooled to ambient temperature, to reduce the solubility of the deb-ranched starch. The precipitate may then be heated to about 70° C., while in contact with a liquid medium, to dissolve at least a portion of the precipitate. Reprecipitation by cooling of the suspension/solution may then be employed. Repeti-tion of the dissolving and the reprecipitation tends to improve the temperature stability of the resulting aqueous dispersion as was observed on repeating the cycle of heating and cooling, a total of 8 times.

In one embodiment, a process for increasing the amount of RS (to a minimum of 15%) in high amylose starch, such as Hylon V or Hylon VII consisted essentially of gelatini-zation of a starch slurry, enzymic debranching of the starch, and isolation of the starch product by extrusion or drying. A further increase in amylase-resistant starch was obtained by addition of an inorganic salt to debranched starch before isolation.

Chemical Treatment

In type IV RS (chemically treated RS), the enzyme resistance is introduced by modifying the starch by cross-linking with chemical agents. Crosslinked starches are obtained by the reaction of starch with bi- or polyfunctional reagents like sodium trimetaphosphate, phosphorus oxy-chloride, or mixed anhydrides of acetic acid and dicarbox-ylic acids like adipic acid. Cross-linking carried out by sulphonate and phosphate groups between various starch molecules involves linking their hydroxyl group thus bring-ing resistance to amylolytic enzyme reaction on the starch molecule (being resistant to digestion).

Distarch phosphates with 0.4% to 0.5% phosphorus have been prepared and they contain both slowly digested starch (SDS) and type IV RS. In some embodiments, the modified starches were obtained in quantitative yield, and provided 13% to 69% of SDS and 18% to 87% RS4. RS4 starches with low swelling power have also been prepared similarly from wheat, corn, waxy corn, high amylose corn, oat, rice tapioca, mung bean, banana, and potato starches.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufac-ture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

Maize RS preparation. In one embodiment, high-amylose maize starches have high gelatinization temperatures, requiring temperatures that are often not reached in conventional cooking practices (154° C. to 171° C.) before the granules are completely disrupted. These starches offer an opportunity to manipulate the amount of RS present in food products.

In one embodiment, RS from maize, corn, pea, wheat, rise, oat, barley, green banana can be produced by first fully hydrating and disrupting the starch granules, followed by an enzymatic debranching of the amylopectin to yield a low dietary fiber maltodextrin mixture, which is almost entirely a straight chain. Then, the mixture is treated through thermal cycles to achieve a high level of retrogradation of type III RS before drying. This can produce 40-95 W % resistant starch content.

In one embodiment, a method includes processes for manufacturing granular forms of concentrated RS containing 47% to 60% RS by heating and cooling high-amylose corn starch under conditions of carefully controlled moisture and temperature. The modification renders the native granule more stable by holding the starch at elevated temperature (60° C. to 160° C.) in the presence of limited water (10% to 80%). Depending on the process, the resulting RS can have melting temperature of 99-125° C., which can be used for different applications, e.g., drinks, cereals, meals, cooking, baking, etc.

In one embodiment, oat beta glucan is produced from oat bran. Enzymes are used to debranch the dietary fiber. Extraction, centrifuging, and alcohol precipitation of the product are included to separate the straight chain amylopectin. The extracted product is then dried, cooled, and milled in the power form of 5-100 □m particle size. This can produce 40-95 W % resistant starch content.

In one embodiment, the green banana RS is produced by baking at 40-80° C. for 2-12 hours. Then the a cooling period is provided. The cooled product is then milled into powder of 5-100 □m particle size. This can produce 40-95 W % resistant starch content.

In one embodiment, a corn or maize RS can be produced by one or more cycles of heating, enzymatic reaction, and cooling. This may produce high concentration (more than 70 w %) of short, straight chain of RS that is soluble in water. Spray drying can be used to produce corn or maize RS powder in the particle size of 5-100 □m.

The followings are aspects of various embodiments of this disclosures.

Aspect 1. A health benefiting daily nutrition includes protein, the protein having a protein weight; and fiber, the fiber having a fiber weight, the fiber weight is more than 5 g, fiber being milled in powder form with particle sizes of 5-400 □m, the fiber having a purity of at least 35 w % resistant starches; wherein a ratio of [the protein weight]:[the fiber weight]=1:0.2-5.

Aspect 2. The health benefiting daily nutrition according to Aspect 1, wherein the fiber includes green banana resistant starch, the green banana resistant starch having a green banana resistant starch weight; maize resistant starch, the maize resistant starch having a maize resistant starch weight; oat beta glucan, the oat beta glucan having a oat beta glucan weight; and corn resistant dextrin, the corn resistant dextrin having a corn resistant dextrin weight, wherein a ratio of [the green banana resistant starch weight]:[the maize resistant starch weight]:[oat beta glucan weight]:[corn resistant dextrin weight]=1:0-2.5:0-2.5:0-2.5.

Aspect 3. The health benefiting daily nutrition according to Aspects 1-2, wherein the fiber consists essentially of: resistant starch, the resistant starch having a resistant starch weight; beta glucan having a beta glucan weight; resistant dextrin having a resistant dextrin weight, wherein a ratio of [the resistant starch weight]:[the beta glucan weight]:[the resistant dextrin weight]=1:0.1-5:0.1-5.

Aspect 4. The health benefiting daily nutrition according to Aspects 1-3, wherein protein weight is more than 5 g.

Aspect 5. The health benefiting daily nutrition according to Aspects 1-4, wherein the protein is one selected from animal protein, vegan protein, or a combination thereof.

Aspect 6. The health benefiting daily nutrition according to Aspects 1-5 further including fat, the fat having a fat weight, wherein a ratio of [the protein weight]:[the fat weight]=1:0-3.0.

Aspect 7. The health benefiting daily nutrition according to Aspects 1-6, wherein the fat is one selected from peanut oil, vegetable oil, avocado oil, olive oil, sunflower oil, safflower oil, flaxseed oil, or a combination thereof.

Aspect 8. The health benefiting daily nutrition according to Aspects 1-7, wherein the protein and fiber are mixed in 8-15 fl oz of water, dairy milk, oat milk, almond milk, pea milk, soy milk, coconut milk, cashew milk, or rice milk.

Aspect 9. A method of producing a health benefiting daily nutrition includes producing protein powders from one or more protein sources, the protein powders having a protein weight; producing fiber powders from one or more fiber sources, the fiber powders having a fiber weight, wherein producing fiber powders including milling and drying the one or more fiber sources, the fiber powders having a particle size of 5-400 □m, the fiber powders including a purity of at least 35 w % of resistant starches; and packing the protein powders and the fiber powders; wherein a ratio of [the protein weight]:[the fiber weight]=1:0.25-3.5.

Aspect 10. The method of Aspect 9, including producing fat powders from one or more fat sources, the fat powders having a fat weight, wherein a ratio of [the protein weight]:[the fat weight]=1:0.1-2.5.

Aspect 11. The method of Aspects 9-10, wherein the fiber powders include green banana resistant starch, the green banana resistant starch having a green banana resistant starch weight; maize resistant starch, the maize resistant starch having a maize resistant starch weight; oat beta glucan, the oat beta glucan having a oat beta glucan weight; and corn resistant dextrin, the corn resistant starch having a corn resistant dextrin weight; wherein a ratio of [the green banana resistant starch weight]:[the maize resistant starch weight]:[oat beta glucan weight]:[corn resistant dextrin weight]=1:0.5-1.5:0.5-1.5:0.5-1.5.

Aspect 12. The method of Aspects 9-11 wherein the fiber powders consist resistant starch, the resistant starch having a resistant starch weight; beta glucan having a beta glucan weight; resistant dextrin having a resistant dextrin weight, wherein a ratio of [the resistant starch weight]:[the beta glucan weight]:[the resistant dextrin weight]=1:0.1-3.5:0.1-3.5.

Aspect 13. The method of Aspects 9-12, wherein fiber weight is more than 5 g.

Aspect 14. The method of Aspects 9-13, wherein the protein source is one selected from animal protein, vegan protein, or a combination thereof.

Aspect 15. The method of Aspects 9-14, wherein producing protein powders from one or more protein sources includes dehydrating the one or more protein source; and crushing, blending, or homogenizing the one or more protein sources.

Aspect 16. A method of facilitating health of a person, comprising identifying a physical condition of the person; providing the person with a daily nutrition that is beneficial to the physical condition, the daily nutrition including: protein, the protein having a protein weight; and fiber, the fiber having a fiber weight, the fiber weight is more than 5 g, fiber being milled in powder form with particle sizes of 5-400 □m, the fiber having a purity of at least 50 w % resistant starches; wherein a ratio of [the protein weight]:[the fiber weight]=1:0.5-2.5.

Aspect 17. The method of Aspect 16, wherein the fiber includes green banana resistant starch, the green banana resistant starch having a green banana resistant starch weight; maize resistant starch, the maize resistant starch having a maize resistant starch weight; oat beta glucan, the oat beta glucan having a oat beta glucan weight; corn resistant dextrin, the corn resistant starch having a corn resistant dextrin weight; wherein a ratio of [the green banana resistant starch weight]:[the maize resistant starch weight]: [oat beta glucan weight]:[corn resistant dextrin weight]=1: 0.5-1.4:0.7-1.4:0.7-1.5.

Aspect 18. The method of Aspects 16-17, wherein the fiber consists essentially of: resistant starch, the resistant starch having a resistant starch weight; beta glucan having a beta glucan weight; resistant dextrin having a resistant dextrin weight, wherein a ratio of [the resistant starch weight]:[the beta glucan weight]:[the resistant dextrin weight]=1:0.15-4:0.15-4.

Aspect 19. The method of Aspects 16-18, wherein the protein weight is more than 5 g.

Aspect 20. The method of Aspects 16-19, wherein the protein is one selected from animal protein, vegan protein, or a combination thereof.

Aspect 21. The method of Aspects 16-20, the daily nutrition further including fat, the fat having a fat weight, wherein a ratio of [the protein weight]:[the fat weight]=1: 0.15-2.

Aspect 22. The method of Aspects 16-21, wherein the physical condition is one selected from the group consisting of: a diabetes, a blood sugar control, a digestive disorder, a microbiome dysbiosis, overweight and obesity, a symptom of menopause, a cardiovascular disease, a mental disorder, a neural disorder, an endocrine disorder, a symptom of aging, a viral infection, a bacterial infection, an immune system disease, and an autoimmunity.

Aspect 23. The method of Aspects 16-22, further including mixing the daily nutrition with 8-15 fl oz of water, dairy milk, oat milk, almond milk, pea milk, soy milk, coconut milk, cashew milk, or rice milk.

Aspect 24. The method of Aspects 16-23, wherein the daily nutrition is in a form of powder, beverage, cookie, dissert, snack bar, bread, pudding, or bakery products.

What is claimed is:

1. A fiber blend for a health benefiting nutrition formulation, comprising:
   a resistant starch obtained from one or more sources selected from the group consisting of green banana resistant starch, maize or corn resistant starch, and potato resistant starch, the resistant starch having a resistant starch weight;
   an oat beta glucan having a beta glucan weight; and
   a maize or corn resistant dextrin having a resistant dextrin weight,
   wherein:
   the ratio of [the resistant starch weight]:[the beta glucan weight]:[the resistant dextrin weight]=1:0.15-4:0.15-4; and
   the fibers are milled in powder form with particle sizes of 5-400 μm.

2. The fiber blend of claim 1, wherein the fiber weight is more than 5 g.

3. The fiber blend of claim 1, wherein the fiber powders have a particle size of 5-100 μm.

4. The fiber blend of claim 1, wherein the resistant starch is obtained from two or more different sources.

5. The fiber blend of claim 1, wherein the ratio of [the resistant starch weight]:[the beta glucan weight]:[the resistant dextrin weight]=1:0.1-3.5:0.1-3.5.

6. The fiber blend of claim 1, wherein the ratio of [the resistant starch weight]:[the beta glucan weight]:[the resistant dextrin weight]=1:0.1-2:0.1-2.

7. The fiber blend of claim 1, wherein the ratio of [the resistant starch weight]:[the beta glucan weight]:[the resistant dextrin weight]=1.25-2.75:0.25-1.75:0.25-1.75.

8. The fiber blend of claim 1, wherein a ratio of [the resistant starch weight]:[the beta glucan weight]:[the resistant dextrin weight]=1.5-2.5:0.5-1.5:0.5-1.5.

9. A health benefiting formulation, in the form of powders, capsules, tablets, cookie, dessert, bars, beverage, bread, pudding, or bakery products, formed from the fiber blend of claim 1.

10. A health benefiting formulation, in the form of a liquid or shake, comprising the fiber blend of claim 1, and a liquid medium.

11. The health benefiting formulation of claim 10, wherein the liquid medium is water, dairy milk, almond milk, oat milk, pea milk, soy milk, coconut milk, cashew milk, or rice milk.

12. A method of facilitating health of a person, comprising identifying a physical condition of the person;
   providing the person with a health benefiting formulation comprising the fiber blend according to claim 1, wherein the health benefiting formulation is beneficial to the physical condition of the person.

13. The method of claim 12, wherein the resistant starch is obtained from two or more different sources.

14. The method of claim 12, wherein the physical condition is one selected from the group consisting of: a diabetes, a blood sugar control, a weight control, a digestive disorder, a microbiome dysbiosis, overweight and obesity, a symptom of menopause, a cardiovascular disease, a mental disorder, a neural disorder, an endocrine disorder, a symptom of aging, a viral infection, a bacterial infection, an immune system disease, and an autoimmunity.

15. The method of claim 14, wherein the physical condition is blood sugar control and/or weight control.

16. The method of claim 12, wherein the fiber blend is provided in a form of powders, capsules, tablets, bars, beverage, cookie, dessert, bread, pudding, or bakery products.

17. The method of claim 12, further comprising mixing the fiber blend with a liquid medium.

18. The method of claim 17, wherein the liquid medium is water, dairy milk, almond milk, oat milk, pea milk, soy milk, coconut milk, cashew milk, or rice milk.

19. The method of claim 12, further comprising mixing the fiber blend with water under the gelatinization temperature.

20. The method of claim 12, further comprising mixing the fiber blend with water under above the gelatinization temperature.

* * * * *